US005936138A

United States Patent [19]
Wieder et al.

[11] Patent Number: 5,936,138
[45] Date of Patent: Aug. 10, 1999

[54] GENE ENCODING MUTANT L3T4 PROTEIN WHICH FACILITATES HIV INFECTION AND TRANSGENIC MOUSE EXPRESSING SUCH PROTEIN

[75] Inventors: Kenneth J. Wieder, Dedham; Terry B. Strom, Brookline, both of Mass.

[73] Assignee: Beth Israel Hospital, Boston, Mass.

[21] Appl. No.: 08/842,657

[22] Filed: Apr. 15, 1997

Related U.S. Application Data

[63] Continuation of application No. 08/222,124, Apr. 4, 1994, Pat. No. 5,620,881, which is a continuation of application No. 08/046,025, Apr. 12, 1993, abandoned, which is a continuation of application No. 07/746,701, Aug. 16, 1991, abandoned.

[51] Int. Cl.$^6$ .............................. C12N 5/00; C12N 15/00; C12N 15/09; C12N 15/63
[52] U.S. Cl. .............................. 800/2; 435/455; 435/462; 435/463; 435/5; 435/320.1; 435/325; 435/69.1; 424/9.21
[58] Field of Search .............................. 800/2; 435/172.3, 435/69.1, 5, 320.1, 325, 455, 462, 463; 424/9.21

[56] References Cited

U.S. PATENT DOCUMENTS 4,873,191 10/1989 Wagner et al. ....................... 435/172.3

FOREIGN PATENT DOCUMENTS

PCT/US92/06827 10/1992 WIPO .

OTHER PUBLICATIONS

Houdebine, Journal of Biotechnology, vol. 34, pp. 269–287, 1994.
Wall, Theriogenology, vol. 45, pp. 57–68, 1996.
Kappel et al., Current Opinion in Biotechnology, vol. 3, pp. 548–553, 1992.
Strojek & Wagner, Genetic Engineering: Principles and Methods, vol. 10, pp. 221–246, 1988.
Wieder et al., Aids Research and Human Retroviruses, vol. 12, pp. 867–876, Jul. 1, 1996.
Littman et al., Nature, vol. 325, Issued Jan. 29, 1987, pp. 453–455.
Moebius et al., J.Exp.Med., vol. 176, Issued Aug. 1992, pp. 507–517.
Piatier–Tonneau et al., Proc.Natl.Acad.Sci. USA, vol. 88, Issued Aug. 1991, pp. 6858–6862.
Arthos et al., Cell 51 : 469–481 (1989).
L. K. Clayton et al., "Substitution of murine for human CD4 residues identifies amino acids critical for HIV–gp120 binding", Nature, vol. 335, Sep., 1988, pp. 363–366.
P. J. Maddon et al., "The Isolation and Nucleotide Sequence of a cDNA Encoding the T Cell Surface Protein T4: A New Member of the Immunoglobulin Gene Family", Cell, vol. 42, Aug., 1985, pp. 93–104.
S. Ryu et al., "Crystal structure of an HIV–binding recombinant fragment of human CD4", Nature, vol. 348, Nov., 1990, pp. 419–426.
D. Camerini et al., "A CD4 Domain Important for HIV–Mediated Syncytium Formation Lies outside the Virus Binding Site", Cell, vol. 60, Mar., 1990, pp. 747–754.
P. J. Maddon et al., "Structure and expression of the human and mouse T4 genes", Proc. Natl. Acad. Sci., vol. 84, Dec., 1987, pp. 9155–9159.
T. Mizukami et al., Binding reg. for hum. imm. vir. (HIV) and epitopes for HIV–blocking monoclonal anti. of the CD4 molecule defined by site–directed mutagenesis, Pro. Nt. Aca. Sci, vol. 85, 1988, pp. 9273–9277.
B. Tourvielle et al., "Isolation and Sequence of L3T4 Complementary DNA Clones: Expression in T Cells and Brain", Science, vol. 23, Oct., 1986, pp. 610–614.
A. Peterson et al., "Genetic Analysis of Monoclonal Antibody and HIV Binding Sites on the Human Lymphocyte Antigen CD4", Cell, vol. 54, Jul., 1988, pp. 65–72.
Q. J. Sattentau et al., "Structural Analysis Of The Human Immunodeficiency Virus–Binding Domain of CD4", J. Exp. Med., vol. 170, Oct., 1989, pp. 1319–1334.
M. H. Brodsky et al., "Analysis Of The Site in CD4 That Binds To The HIV Envelope Glycoprotein", The Journal of Immunology, vol. 144, No. 8, Apr., 1990, pp. 3078–3086.
J. Arthos et al., "Identification of the Residues in Human CD4 Critical for the Binding of HIV", Cell, vol. 57, May, 1989, pp. 469–480.
P. J. Maddon et al., "The T4 Gene Encodes the AIDS Virus Receptor and Is Expressed in the Immune System and the Brain", Cell, vol. 47, Nov., 1986, pp. 333–348.
N. R. Landau et al., "The envelope glycoprotein of the human immunodeficiency virus binds to the immunoglobulin–like domain of CD4", Nature, vol. 334, Jul., 1988, pp. 159–165.
P. Bedinger et al., "Internalization of the human immunodeficiency virus does not require the cytoplasmic domain of CD4", Nature, vol. 334, Jul. 1988, pp. 162–165.
Littman et al., Nature 325 : 453–455 (1987).
Maddon et al., PNAS 84 : 9155–9159 (1987).
Clayton et al., Nature 335 : 362–366 (1988).
Ryu et al., Nature 348 : 419–425 (1990).

*Primary Examiner*—Jasemine C. Chambers
*Assistant Examiner*—Jill D. Martin
*Attorney, Agent, or Firm*—Fish & Richardson P.C.

[57] ABSTRACT

Disclosed are (1) a DNA sequence encoding a mutant L3T4 protein which, when expressed on the surface of a cell, is capable of facilitating infection of the cell by human immunodeficiency virus; the mutant protein includes at least one amino acid residue substitution or deletion in a segment corresponding to the gp120 binding epitope of a native L3T4 protein so as to increase homology between that segment and its counterpart in a CD4 protein; (2) a murine cell line or strain transfected with such a DNA sequence; and (3) a transgenic mouse susceptible to infection by human immunodeficiency virus.

23 Claims, 13 Drawing Sheets

```
GCTCAGATTC CCAACCAACA AGAGCTCAAG GAGACCACC                                                    39

ATG TGC CGA GCC ATC TCT CTT AGG CGC TTG CTG CTG CTG CTG CTG CAG                              87
Met Cys Arg Ala Ile Ser Leu Arg Arg Leu Leu Leu Leu Leu Leu Gln
                        -20

CTG TCA CAA CTC CTA GCT GTC ACT CAA GGG AAG ACG CTG GTG CTG GGG                              135
Leu Ser Gln Leu Leu Ala Val Thr Gln Gly Lys Thr Leu Val Leu Gly
-10                                        -1  +1

AAG GAA GGG GAA TCA GCA GAA CTG CCC TGC GAG AGT TCC CAG AAG AAG                              183
Lys Glu Gly Glu Ser Ala Glu Leu Pro Cys Glu Ser Ser Gln Lys Lys
                10                                      20

ATC ACA GTC TTC ACC TGG AAG TTC TCT GAC CAG AGG AAG ATT CTG GGG                              231
Ile Thr Val Phe Thr Trp Lys Phe Ser Asp Gln Arg Lys Ile Leu Gly
                        30

CAG CAT GGC AAA GGT GTA TTA ATT AGA GGA CCT TCG AAG TTG AAC ---                              279
Gln His Gly Lys Gly Val Leu Ile Arg Gly Pro Ser Lys Leu Asn ---
        40                                      50

GAT CGT TTT GAT TCC AAA AAA GGG GCA TGG GAG AAA GGA TCG TTT CCT                              327
Asp Arg Phe Asp Ser Lys Lys Gly Ala Trp Glu Lys Gly Ser Phe Pro
                    60                                          70

CTC ATC ATC AAT AAA CTT AAG ATG GAA GAC TCT CAG ACT TAT ATC TGT                              375
Leu Ile Ile Asn Lys Leu Lys Met Glu Asp Ser Gln Thr Tyr Ile Cys
                                    80

GAG CTG GAG AAC AGG AAA GAG GAG GTG GAG TTG TGG GTG TTC AAA GTG                              423
Glu Leu Glu Asn Arg Lys Glu Glu Val Glu Leu Trp Val Phe Lys Val
                90                                      100

ACC TTC AGT CCG GGT ACC AGC CTG TTG CAA GGG CAG AGC CTG ACC CTG                              471
Thr Phe Ser Pro Gly Thr Ser Leu Leu Gln Gly Gln Ser Leu Thr Leu
                            110

ACC TTG GAT AGC AAC TCT AAG GTC TCT AAC CCC TTG ACA GAG TGC AAA                              519
Thr Leu Asp Ser Asn Ser Lys Val Ser Asn Pro Leu Thr Glu Cys Lys
        120                                     130

CAC AAA AAG GGT AAA GTT GTC AGT GGT TCC AAA GTT CTC TCC ATG TCC                              567
His Lys Lys Gly Lys Val Val Ser Gly Ser Lys Val Leu Ser Met Ser
                    140                                         150

AAC CTA AGG GTT CAG GAC AGC GAC TTC TGG AAC TGC ACC GTG ACC CTG                              615
Asn Leu Arg Val Gln Asp Ser Asp Phe Trp Asn Cys Thr Val Thr Leu
                                160
```

FIG. 1A

```
GAC CAG AAA AAG AAC TGG TTC GGC ATG ACA CTC TCA GTG CTG GGT TTT     663
Asp Gln Lys Lys Asn Trp Phe Gly Met Thr Leu Ser Val Leu Gly Phe
            170                                     180

CAG AGC ACA GCT ATC ACG GCC TAT AAG AGT GAG GGA GAG TCA GCG GAG     711
Gln Ser Thr Ala Ile Thr Ala Tyr Lys Ser Glu Gly Glu Ser Ala Glu
                        190

TTC TCC TTC CCA CTC AAC TTT GCA GAG GAA AAC GGG TGG GGA GAG CTG     759
Phe Ser Phe Pro Leu Asn Phe Ala Glu Glu Asn Gly Trp Gly Glu Leu
    200                                     210

ATG TGG AAG GCA GAG AAG GAT TCT TTC TTC CAG CCC TGG ATC TCC TTC     807
Met Trp Lys Ala Glu Lys Asp Ser Phe Phe Gln Pro Trp Ile Ser Phe
                    220                                     230

TCC ATA AAG AAC AAA GAG GTG TCC GTA CAA AAG TCC ACC AAA GAC CTC     855
Ser Ile Lys Asn Lys Glu Val Ser Val Gln Lys Ser Thr Lys Asp Leu
                                    240

AAG CTC CAG CTG AAG GAA ACG CTC CCA CTC ACC CTC AAG ATA CCC CAG     903
Lys Leu Gln Leu Lys Glu Thr Leu Pro Leu Thr Leu Lys Ile Pro Gln
            250                                     260

GTC TCG CTT CAG TTT GCT GGT TCT GGC AAC CTG ACT CTG ACT CTG GAC     951
Val Ser Leu Gln Phe Ala Gly Ser Gly Asn Leu Thr Leu Thr Leu Asp
                            270

AAA GGG ACA CTG CAT CAG GAA GTG AAC CTG GTG GTG ATG AAA GTG GCT     999
Lys Gly Thr Leu His Gln Glu Val Asn Leu Val Val Met Lys Val Ala
        280                                     290

CAG CTC AAC AAT ACT TTG ACC TGT GAG GTG ATG GGA CCT ACC TCT CCC   1,047
Gln Leu Asn Asn Thr Leu Thr Cys Glu Val Met Gly Pro Thr Ser Pro
                        300                                     310

AAG ATG AGA CTG ACC CTG AAG CAG GAG AAC CAG GAG GCC AGG GTC TCT   1,095
Lys Met Arg Leu Thr Leu Lys Gln Glu Asn Gln Glu Ala Arg Val Ser
                                    320

GAG GAG CAG AAA GTA GTT CAA GTG GTG GCC CCT GAG ACA GGG CTG TGG   1,143
Glu Glu Gln Lys Val Val Gln Val Val Ala Pro Glu Thr Gly Leu Trp
            330                                     340

CAG TGT CTA CTG AGT GAA GGT GAT AAG GTC AAG ATG GAC TCC AGG ATC   1,191
Gln Cys Leu Leu Ser Glu Gly Asp Lys Val Lys Met Asp Ser Arg Ile
                        350
```

FIG. 1B

```
CAG GTT TTA TCC AGA GGG GTG AAC CAG ACA GTG TTC CTG GCT TGC GTG   1,239
Gln Val Leu Ser Arg Gly Val Asn Gln Thr Val Phe Leu Ala Cys Val
    360                                     370

CTG GGT GGC TCC TTC GGC TTT CTG GGT TTC CTT GGG CTC TGC ATC CTC   1,287
Leu Gly Gly Ser Phe Gly Phe Leu Gly Phe Leu Gly Leu Cys Ile Leu
                    380                                     390

TGC TGT GTC AGG TGC CGG CAC CAA CAG CGC CAG GCA GCA CGA ATG TCT   1,335
Cys Cys Val Arg Cys Arg His Gln Gln Arg Gln Ala Ala Arg Met Ser
                                    400

CAG ATC AAG AGG CTC CTC AGT GAG AAG AAG ACC TGC CAG TGC CCC CAC   1,383
Gln Ile Lys Arg Leu Leu Ser Glu Lys Lys Thr Cys Gln Cys Pro His
            410                                     420

CGG ATG CAG AAG AGC CAT AAT CTC ATC TGA GGCC    (SEQ ID NO:9)     1,417
Arg Met Gln Lys Ser His Asn Leu Ile
                        430
```

FIG. 1C

```
GCTCAGATTC CCAACCAACA AGAGCTCAAG GAGACCACC                                    39

ATG TGC CGA GCC ATC TCT CTT AGG CGC TTG CTG CTG CTG CTG CTG CAG              87
Met Cys Arg Ala Ile Ser Leu Arg Arg Leu Leu Leu Leu Leu Leu Gln
                        -20

CTG TCA CAA CTC CTA GCT GTC ACT CAA GGG AAG ACG CTG GTG CTG GGG             135
Leu Ser Gln Leu Leu Ala Val Thr Gln Gly Lys Thr Leu Val Leu Gly
-10                                       -1  +1

AAG GAA GGG GAA TCA GCA GAA CTG CCC TGC GAG AGT TCC CAG AAG AAG             183
Lys Glu Gly Glu Ser Ala Glu Leu Pro Cys Glu Ser Ser Gln Lys Lys
                10                                      20

ATC ACA GTC TTC ACC TGG AAG TTC TCT GAC CAG AGG AAG ATT CTG GGG             231
Ile Thr Val Phe Thr Trp Lys Phe Ser Asp Gln Arg Lys Ile Leu Gly
                        30

AAC CAA GGC --- TCT TTC TTA ATT AGA GGA CCT TCG AAG TTG AAC ---             279
Asn Gln Gly --- Ser Phe Leu Ile Arg Gly Pro Ser Lys Leu Asn ---
        40                                      50

GAT CGT GCT GAT TCC AAA AAA GGG GCA TGG GAG AAA GGA TCG TTT CCT             327
Asp Arg Ala Asp Ser Lys Lys Gly Ala Trp Glu Lys Gly Ser Phe Pro
                        60                                      70

CTC ATC ATC AAT AAA CTT AAG ATG GAA GAC TCT CAG ACT TAT ATC TGT             375
Leu Ile Ile Asn Lys Leu Lys Met Glu Asp Ser Gln Thr Tyr Ile Cys
                                80

GAG CTG GAG AAC AGG AAA GAG GAG GTG GAG TTG TGG GTG TTC AAA GTG             423
Glu Leu Glu Asn Arg Lys Glu Glu Val Glu Leu Trp Val Phe Lys Val
                90                                      100

ACC TTC AGT CCG GGT ACC AGC CTG TTG CAA GGG CAG AGC CTG ACC CTG             471
Thr Phe Ser Pro Gly Thr Ser Leu Leu Gln Gly Gln Ser Leu Thr Leu
                                110

ACC TTG GAT AGC CCC CCT GGG --- TCT AAC CCC TTG ACA GAG TGC AAA             519
Thr Leu Asp Ser Pro Pro Gly --- Ser Asn Pro Leu Thr Glu Cys Lys
            120                                     130

CAC AAA AAG GGT AAA GTT GTC AGT GGT TCC AAA GTT CTC TCC ATG TCC             567
His Lys Lys Gly Lys Val Val Ser Gly Ser Lys Val Leu Ser Met Ser
                    140                                     150

AAC CTA AGG GTT CAG GAC AGC GGC ACC TGG ACC TGC ACC GTG ACC CTG             615
Asn Leu Arg Val Gln Asp Ser Gly Thr Trp Thr Cys Thr Val Thr Leu
                                160
```

FIG. 2A

| | | | | | | | | | | | | | | | | |
|---|---|---|---|---|---|---|---|---|---|---|---|---|---|---|---|---|
| GAC | CAG | AAA | AAG | AAC | TGG | TTC | GGC | ATG | ACA | CTC | TCA | GTG | CTG | GGT | TTT | 663 |
| Asp | Gln | Lys | Lys | Asn | Trp | Phe | Gly | Met | Thr | Leu | Ser | Val | Leu | Gly | Phe | |
| | | | 170 | | | | | | | | | | 180 | | | |
| CAG | AGC | ACA | GCT | ATC | ACG | GCC | TAT | AAG | AGT | GAG | GGA | GAG | TCA | GCG | GAG | 711 |
| Gln | Ser | Thr | Ala | Ile | Thr | Ala | Tyr | Lys | Ser | Glu | Gly | Glu | Ser | Ala | Glu | |
| | | | | | | | | 190 | | | | | | | | |
| TTC | TCC | TTC | CCA | CTC | AAC | TTT | GCA | GAG | GAA | AAC | GGG | TGG | GGA | GAG | CTG | 759 |
| Phe | Ser | Phe | Pro | Leu | Asn | Phe | Ala | Glu | Glu | Asn | Gly | Trp | Gly | Glu | Leu | |
| | | 200 | | | | | | | | | | 210 | | | | |
| ATG | TGG | AAG | GCA | GAG | AAG | GAT | TCT | TTC | TTC | CAG | CCC | TGG | ATC | TCC | TTC | 807 |
| Met | Trp | Lys | Ala | Glu | Lys | Asp | Ser | Phe | Phe | Gln | Pro | Trp | Ile | Ser | Phe | |
| | | | | | 220 | | | | | | | | | | 230 | |
| TCC | ATA | AAG | AAC | AAA | GAG | GTG | TCC | GTA | CAA | AAG | TCC | ACC | AAA | GAC | CTC | 855 |
| Ser | Ile | Lys | Asn | Lys | Glu | Val | Ser | Val | Gln | Lys | Ser | Thr | Lys | Asp | Leu | |
| | | | | | | | | | 240 | | | | | | | |
| AAG | CTC | CAG | CTG | AAG | GAA | ACG | CTC | CCA | CTC | ACC | CTC | AAG | ATA | CCC | CAG | 903 |
| Lys | Leu | Gln | Leu | Lys | Glu | Thr | Leu | Pro | Leu | Thr | Leu | Lys | Ile | Pro | Gln | |
| | | | 250 | | | | | | | | | | 260 | | | |
| GTC | TCG | CTT | CAG | TTT | GCT | GGT | TCT | GGC | AAC | CTG | ACT | CTG | ACT | CTG | GAC | 951 |
| Val | Ser | Leu | Gln | Phe | Ala | Gly | Ser | Gly | Asn | Leu | Thr | Leu | Thr | Leu | Asp | |
| | | | | | | | | 270 | | | | | | | | |
| AAA | GGG | ACA | CTG | CAT | CAG | GAA | GTG | AAC | CTG | GTG | GTG | ATG | AAA | GTG | GCT | 999 |
| Lys | Gly | Thr | Leu | His | Gln | Glu | Val | Asn | Leu | Val | Val | Met | Lys | Val | Ala | |
| | | 280 | | | | | | | | | | 290 | | | | |
| CAG | CTC | AAC | AAT | ACT | TTG | ACC | TGT | GAG | GTG | ATG | GGA | CCT | ACC | TCT | CCC | 1,047 |
| Gln | Leu | Asn | Asn | Thr | Leu | Thr | Cys | Glu | Val | Met | Gly | Pro | Thr | Ser | Pro | |
| | | | | 300 | | | | | | | | | | | 310 | |
| AAG | ATG | AGA | CTG | ACC | CTG | AAG | CAG | GAG | AAC | CAG | GAG | GCC | AGG | GTC | TCT | 1,095 |
| Lys | Met | Arg | Leu | Thr | Leu | Lys | Gln | Glu | Asn | Gln | Glu | Ala | Arg | Val | Ser | |
| | | | | | | | | | 320 | | | | | | | |
| GAG | GAG | CAG | AAA | GTA | GTT | CAA | GTG | GTG | GCC | CCT | GAG | ACA | GGG | CTG | TGG | 1,143 |
| Glu | Glu | Gln | Lys | Val | Val | Gln | Val | Val | Ala | Pro | Glu | Thr | Gly | Leu | Trp | |
| | | | 330 | | | | | | | | | | 340 | | | |
| CAG | TGT | CTA | CTG | AGT | GAA | GGT | GAT | AAG | GTC | AAG | ATG | GAC | TCC | AGG | ATC | 1,191 |
| Gln | Cys | Leu | Leu | Ser | Glu | Gly | Asp | Lys | Val | Lys | Met | Asp | Ser | Arg | Ile | |
| | | | | | | 350 | | | | | | | | | | |

FIG. 2B

```
CAG GTT TTA TCC AGA GGG GTG AAC CAG ACA GTG TTC CTG GCT TGC GTG    1,239
Gln Val Leu Ser Arg Gly Val Asn Gln Thr Val Phe Leu Ala Cys Val
        360                             370

CTG GGT GGC TCC TTC GGC TTT CTG GGT TTC CTT GGG CTC TGC ATC CTC    1,287
Leu Gly Gly Ser Phe Gly Phe Leu Gly Phe Leu Gly Leu Cys Ile Leu
                    380                             390

TGC TGT GTC AGG TGC CGG CAC CAA CAG CGC CAG GCA GCA CGA ATG TCT    1,335
Cys Cys Val Arg Cys Arg His Gln Gln Arg Gln Ala Ala Arg Met Ser
                                    400

CAG ATC AAG AGG CTC CTC AGT GAG AAG AAG ACC TGC CAG TGC CCC CAC    1,383
Gln Ile Lys Arg Leu Leu Ser Glu Lys Lys Thr Cys Gln Cys Pro His
        410                             420

CGG ATG CAG AAG AGC CAT AAT CTC ATC TGA GGCC   (SEQ ID NO:10)      1,417
Arg Met Gln Lys Ser His Asn Leu Ile
                    430
```

FIG. 2C

COS Mock L3T4 M1 M5 M6 CD4

COS Mock L3T4 M1 M5 M6 CD4

```
                         SEQUENCE LISTING (1) GENERAL INFORMATION:

(iii) NUMBER OF SEQUENCES:        10

(2) INFORMATION FOR SEQ ID NO:1:

(i) SEQUENCE CHARACTERISTICS:
          (A) LENGTH:                5
          (B) TYPE:                  amino acid
          (D) TOPOLOGY:              linear (xi) SEQUENCE DESCRIPTION: SEQ ID NO:1:

Pro Ser Lys Leu Asn
                5

(2) INFORMATION FOR SEQ ID NO:2:
```

(i) SEQUENCE CHARACTERISTICS:
            (A) LENGTH:           5
            (B) TYPE:             amino acid
            (D) TOPOLOGY:         linear (xi) SEQUENCE DESCRIPTION: SEQ ID NO:2:

Asn Gln Gly Ser Phe
                  5

(2) INFORMATION FOR SEQ ID NO:3:

(i) SEQUENCE CHARACTERISTICS:
            (A) LENGTH:           4
            (B) TYPE:             amino acid
            (D) TOPOLOGY:         linear (xi) SEQUENCE DESCRIPTION: SEQ ID NO:3:

Gly Thr Trp Thr (2) INFORMATION FOR SEQ ID NO:4:

(i) SEQUENCE CHARACTERISTICS:
            (A) LENGTH:           45
            (B) TYPE:             nucleic acid
            (C) STRANDEDNESS:     single
            (D) TOPOLOGY:         linear (xi) SEQUENCE DESCRIPTION: SEQ ID NO:4:

GGAATCAAAA CGATCGTTCA ACTTCGAAGG TCCTCTAATT AATAC                    45

(2) INFORMATION FOR SEQ ID NO:5:

(i) SEQUENCE CHARACTERISTICS:
            (A) LENGTH:           39
            (B) TYPE:             nucleic acid
            (C) STRANDEDNESS:     single
            (D) TOPOLOGY:         linear (xi) SEQUENCE DESCRIPTION: SEQ ID NO:5:

TGTCAAGGGG TTAGACCCAG GGGGGCTATC CAAGGTCAG                           39

(2) INFORMATION FOR SEQ ID NO:6:

(i) SEQUENCE CHARACTERISTICS:
            (A) LENGTH:           36
            (B) TYPE:             nucleic acid
            (C) STRANDEDNESS:     single
            (D) TOPOLOGY:         linear (xi) SEQUENCE DESCRIPTION: SEQ ID NO:6:

GGTCACGGTG CAGGTCCAGG TGCCGCTGTC CTGAAC                              36

(2) INFORMATION FOR SEQ ID NO:7:

(i) SEQUENCE CHARACTERISTICS:
            (A) LENGTH:           45
            (B) TYPE:             nucleic acid
            (C) STRANDEDNESS:     single
            (D) TOPOLOGY:         linear (xi) SEQUENCE DESCRIPTION: SEQ ID NO:7:

CGAAGGTCCT CTAATTAAGA AAGAGCCTTG GTTCCCCAGA ATCTT                    45

(2) INFORMATION FOR SEQ ID NO:8:

(i) SEQUENCE CHARACTERISTICS:
            (A) LENGTH:           27
            (B) TYPE:             nucleic acid

```
              (C) STRANDEDNESS:         single
              (D) TOPOLOGY:             linear (xi) SEQUENCE DESCRIPTION: SEQ ID NO:8:

TTTTTTGGAA TCAGCACGAT CGTTCAA                                            27

(2) INFORMATION FOR SEQ ID NO:9:

(i) SEQUENCE CHARACTERISTICS:
              (A) LENGTH:               1414
              (B) TYPE:                 nucleic acid
              (C) STRANDEDNESS:         single
              (D) TOPOLOGY:             linear (xi) SEQUENCE DESCRIPTION: SEQ ID NO:9:

GCTCAGATTC CCAACCAACA AGAGCTCAAG GAGACCACC ATG TGC CGA GCC ATC            54
                                           Met Cys Arg Ala Ile
                                            -25

TCT CTT AGG CGC TTG CTG CTG CTG CTG CAG CTG TCA CAA CTC CTA              102
Ser Leu Arg Arg Leu Leu Leu Leu Leu Gln Leu Ser Gln Leu Leu
    -20                 -15                 -10

GCT GTC ACT CAA GGG AAG ACG CTG GTG CTG GGG AAG GAA GGG GAA TCA          150
Ala Val Thr Gln Gly Lys Thr Leu Val Leu Gly Lys Glu Gly Glu Ser
 -5                  1               5                  10

GCA GAA CTG CCC TGC GAG AGT TCC CAG AAG AAG ATC ACA GTC TTC ACC          198
Ala Glu Leu Pro Cys Glu Ser Ser Gln Lys Lys Ile Thr Val Phe Thr
                 15                  20                  25

TGG AAG TTC TCT GAC CAG AGG AAG ATT CTG GGG CAG CAT GGC AAA GGT          246
Trp Lys Phe Ser Asp Gln Arg Lys Ile Leu Gly Gln His Gly Lys Gly
         30                  35                  40

GTA TTA ATT AGA GGA CCT TCG AAG TTG AAC GAT CGT TTT GAT TCC AAA          294
Val Leu Ile Arg Gly Pro Ser Lys Leu Asn Asp Arg Phe Asp Ser Lys
     45                  50                  55

AAA GGG GCA TGG GAG AAA GGA TCG TTT CCT CTC ATC ATC AAT AAA CTT          342
Lys Gly Ala Trp Glu Lys Gly Ser Phe Pro Leu Ile Ile Asn Lys Leu
 60                  65                  70                  75

AAG ATG GAA GAC TCT CAG ACT TAT ATC TGT GAG CTG GAG AAC AGG AAA          390
Lys Met Glu Asp Ser Gln Thr Tyr Ile Cys Glu Leu Glu Asn Arg Lys
                 80                  85                  90

GAG GAG GTG GAG TTG TGG GTG TTC AAA GTG ACC TTC AGT CCG GGT ACC          438
Glu Glu Val Glu Leu Trp Val Phe Lys Val Thr Phe Ser Pro Gly Thr
         95                 100                 105

AGC CTG TTG CAA GGG CAG AGC CTG ACC CTG ACC TTG GAT AGC AAC TCT          486
Ser Leu Leu Gln Gly Gln Ser Leu Thr Leu Thr Leu Asp Ser Asn Ser
     110                 115                 120

AAG GTC TCT AAC CCC TTG ACA GAG TGC AAA CAC AAA AAG GGT AAA GTT          534
Lys Val Ser Asn Pro Leu Thr Glu Cys Lys His Lys Lys Gly Lys Val
 125                 130                 135

GTC AGT GGT TCC AAA GTT CTC TCC ATG TCC AAC CTA AGG GTT CAG GAC          582
Val Ser Gly Ser Lys Val Leu Ser Met Ser Asn Leu Arg Val Gln Asp
140                 145                 150                 155

AGC GAC TTC TGG AAC TGC ACC GTG ACC CTG GAC CAG AAA AAG AAC TGG          630
Ser Asp Phe Trp Asn Cys Thr Val Thr Leu Asp Gln Lys Lys Asn Trp
                 160                 165                 170

TTC GGC ATG ACA CTC TCA GTG CTG GGT TTT CAG AGC ACA GCT ATC ACG          678
Phe Gly Met Thr Leu Ser Val Leu Gly Phe Gln Ser Thr Ala Ile Thr
         175                 180                 185

GCC TAT AAG AGT GAG GGA GAG TCA GCG GAG TTC TCC TTC CCA CTC AAC          726
Ala Tyr Lys Ser Glu Gly Glu Ser Ala Glu Phe Ser Phe Pro Leu Asn
     190                 195                 200

TTT GCA GAG GAA AAC GGG TGG GGA GAG CTG ATG TGG AAG GCA GAG AAG          774
Phe Ala Glu Glu Asn Gly Trp Gly Glu Leu Met Trp Lys Ala Glu Lys
```

-continued

```
            205                 210                 215
GAT TCT TTC TTC CAG CCC TGG ATC TCC TTC TCC ATA AAG AAC AAA GAG        822
Asp Ser Phe Phe Gln Pro Trp Ile Ser Phe Ser Ile Lys Asn Lys Glu
220             225                 230                 235

GTG TCC GTA CAA AAG TCC ACC AAA GAC CTC AAG CTC CAG CTG AAG GAA        870
Val Ser Val Gln Lys Ser Thr Lys Asp Leu Lys Leu Gln Leu Lys Glu
                240                 245                 250

ACG CTC CCA CTC ACC CTC AAG ATA CCC CAG GTC TCG CTT CAG TTT GCT        918
Thr Leu Pro Leu Thr Leu Lys Ile Pro Gln Val Ser Leu Gln Phe Ala
                    255                 260                 265

GGT TCT GGC AAC CTG ACT CTG ACT CTG GAC AAA GGG ACA CTG CAT CAG        966
Gly Ser Gly Asn Leu Thr Leu Thr Leu Asp Lys Gly Thr Leu His Gln
            270                 275                 280

GAA GTG AAC CTG GTG GTG ATG AAA GTG GCT CAG CTC AAC AAT ACT TTG       1014
Glu Val Asn Leu Val Val Met Lys Val Ala Gln Leu Asn Asn Thr Leu
285                 290                 295

ACC TGT GAG GTG ATG GGA CCT ACC TCT CCC AAG ATG AGA CTG ACC CTG       1062
Thr Cys Glu Val Met Gly Pro Thr Ser Pro Lys Met Arg Leu Thr Leu
300                 305                 310                 315

AAG CAG GAG AAC CAG GAG GCC AGG GTC TCT GAG GAG CAG AAA GTA GTT       1110
Lys Gln Glu Asn Gln Glu Ala Arg Val Ser Glu Glu Gln Lys Val Val
                320                 325                 330

CAA GTG GTG GCC CCT GAG ACA GGG CTG TGG CAG TGT CTA CTG AGT GAA       1158
Gln Val Val Ala Pro Glu Thr Gly Leu Trp Gln Cys Leu Leu Ser Glu
            335                 340                 345

GGT GAT AAG GTC AAG ATG GAC TCC AGG ATC CAG GTT TTA TCC AGA GGG       1206
Gly Asp Lys Val Lys Met Asp Ser Arg Ile Gln Val Leu Ser Arg Gly
        350                 355                 360

GTG AAC CAG ACA GTG TTC CTG GCT TGC GTG CTG GGT GGC TCC TTC GGC       1254
Val Asn Gln Thr Val Phe Leu Ala Cys Val Leu Gly Gly Ser Phe Gly
365                 370                 375

TTT CTG GGT TTC CTT GGG CTC TGC ATC CTC TGC TGT GTC AGG TGC CGG       1302
Phe Leu Gly Phe Leu Gly Leu Cys Ile Leu Cys Cys Val Arg Cys Arg
380                 385                 390                 395

CAC CAA CAG CGC CAG GCA GCA CGA ATG TCT CAG ATC AAG AGG CTC CTC       1350
His Gln Gln Arg Gln Ala Ala Arg Met Ser Gln Ile Lys Arg Leu Leu
                400                 405                 410

AGT GAG AAG AAG ACC TGC CAG TGC CCC CAC CGG ATG CAG AAG AGC CAT       1398
Ser Glu Lys Lys Thr Cys Gln Cys Pro His Arg Met Gln Lys Ser His
            415                 420                 425

AAT CTC ATC   T GAGGCC                                                 1414
Asn Leu Ile
        430
```

(2) INFORMATION FOR SEQ ID NO:10:

(i) SEQUENCE CHARACTERISTICS:
        (A) LENGTH:                1408
        (B) TYPE:                  nucleic acid
        (C) STRANDEDNESS:      single
        (D) TOPOLOGY:            linear (xi) SEQUENCE DESCRIPTION: SEQ ID NO:10:

```
GCTCAGATTC CCAACCAACA AGAGCTCAAG GAGACCACC ATG TGC CGA GCC ATC         54
                                           Met Cys Arg Ala Ile
                                               -25

TCT CTT AGG CGC TTG CTG CTG CTG CTG CTG CAG CTG TCA CAA CTC CTA       102
Ser Leu Arg Arg Leu Leu Leu Leu Leu Leu Gln Leu Ser Gln Leu Leu
    -20                 -15                 -10

GCT GTC ACT CAA GGG AAG ACG CTG GTG CTG GGG AAG GAA GGG GAA TCA       150
Ala Val Thr Gln Gly Lys Thr Leu Val Leu Gly Lys Glu Gly Glu Ser
 -5                   1                  5                 10
```

```
GCA GAA CTG CCC TGC GAG AGT TCC CAG AAG AAG ATC ACA GTC TTC ACC        198
Ala Glu Leu Pro Cys Glu Ser Ser Gln Lys Lys Ile Thr Val Phe Thr
         15                  20                  25

TGG AAG TTC TCT GAC CAG AGG AAG ATT CTG GGG AAC CAA GGC TCT TTC        246
Trp Lys Phe Ser Asp Gln Arg Lys Ile Leu Gly Asn Gln Gly Ser Phe
         30                  35                  40

TTA ATT AGA GGA CCT TCG AAG TTG AAC GAT CGT GCT GAT TCC AAA AAA        294
Leu Ile Arg Gly Pro Ser Lys Leu Asn Asp Arg Ala Asp Ser Lys Lys
         45                  50                  55

GGG GCA TGG GAG AAA GGA TCG TTT CCT CTC ATC ATC AAT AAA CTT AAG        342
Gly Ala Trp Glu Lys Gly Ser Phe Pro Leu Ile Ile Asn Lys Leu Lys
 60          65                  70                  75

ATG GAA GAC TCT CAG ACT TAT ATC TGT GAG CTG GAG AAC AGG AAA GAG        390
Met Glu Asp Ser Gln Thr Tyr Ile Cys Glu Leu Glu Asn Arg Lys Glu
                 80                  85                  90

GAG GTG GAG TTG TGG GTG TTC AAA GTG ACC TTC AGT CCG GGT ACC AGC        438
Glu Val Glu Leu Trp Val Phe Lys Val Thr Phe Ser Pro Gly Thr Ser
             95                 100                 105

CTG TTG CAA GGG CAG AGC CTG ACC CTG ACC TTG GAT AGC CCC CCT GGG        486
Leu Leu Gln Gly Gln Ser Leu Thr Leu Thr Leu Asp Ser Pro Pro Gly
            110                 115                 120

TCT AAC CCC TTG ACA GAG TGC AAA CAC AAA AAG GGT AAA GTT GTC AGT        534
Ser Asn Pro Leu Thr Glu Cys Lys His Lys Lys Gly Lys Val Val Ser
        125                 130                 135

GGT TCC AAA GTT CTC TCC ATG TCC AAC CTA AGG GTT CAG GAC AGC GGC        582
Gly Ser Lys Val Leu Ser Met Ser Asn Leu Arg Val Gln Asp Ser Gly
140                 145                 150                 155

ACC TGG ACC TGC ACC GTG ACC CTG GAC CAG AAA AAG AAC TGG TTC GGC        630
Thr Trp Thr Cys Thr Val Thr Leu Asp Gln Lys Lys Asn Trp Phe Gly
                160                 165                 170

ATG ACA CTC TCA GTG CTG GGT TTT CAG AGC ACA GCT ATC ACG GCC TAT        678
Met Thr Leu Ser Val Leu Gly Phe Gln Ser Thr Ala Ile Thr Ala Tyr
            175                 180                 185

AAG AGT GAG GGA GAG TCA GCG GAG TTC TCC TTC CCA CTC AAC TTT GCA        726
Lys Ser Glu Gly Glu Ser Ala Glu Phe Ser Phe Pro Leu Asn Phe Ala
        190                 195                 200

GAG GAA AAC GGG TGG GGA GAG CTG ATG TGG AAG GCA GAG AAG GAT TCT        774
Glu Glu Asn Gly Trp Gly Glu Leu Met Trp Lys Ala Glu Lys Asp Ser
205                 210                 215

TTC TTC CAG CCC TGG ATC TCC TTC TCC ATA AAG AAC AAA GAG GTG TCC        822
Phe Phe Gln Pro Trp Ile Ser Phe Ser Ile Lys Asn Lys Glu Val Ser
220                 225                 230                 235

GTA CAA AAG TCC ACC AAA GAC CTC AAG CTC CAG CTG AAG GAA ACG CTC        870
Val Gln Lys Ser Thr Lys Asp Leu Lys Leu Gln Leu Lys Glu Thr Leu
                240                 245                 250

CCA CTC ACC CTC AAG ATA CCC CAG GTC TCG CTT CAG TTT GCT GGT TCT        918
Pro Leu Thr Leu Lys Ile Pro Gln Val Ser Leu Gln Phe Ala Gly Ser
            255                 260                 265

GGC AAC CTG ACT CTG ACT CTG GAC AAA GGG ACA CTG CAT CAG GAA GTG        966
Gly Asn Leu Thr Leu Thr Leu Asp Lys Gly Thr Leu His Gln Glu Val
        270                 275                 280

AAC CTG GTG GTG ATG AAA GTG GCT CAG CTC AAC AAT ACT TTG ACC TGT       1014
Asn Leu Val Val Met Lys Val Ala Gln Leu Asn Asn Thr Leu Thr Cys
285                 290                 295

GAG GTG ATG GGA CCT ACC TCT CCC AAG ATG AGA CTG ACC CTG AAG CAG       1062
Glu Val Met Gly Pro Thr Ser Pro Lys Met Arg Leu Thr Leu Lys Gln
300                 305                 310                 315

GAG AAC CAG GAG GCC AGG GTC TCT GAG GAG CAG AAA GTA GTT CAA GTG       1110
Glu Asn Gln Glu Ala Arg Val Ser Glu Glu Gln Lys Val Val Gln Val
                320                 325                 330
```

| | | | | | | | | | | | | | | |
|---|---|---|---|---|---|---|---|---|---|---|---|---|---|---|
|GTG|GCC|CCT|GAG|ACA|GGG|CTG|TGG|CAG|TGT|CTA|CTG|AGT|GAA|GGT|GAT|1158|
|Val|Ala|Pro|Glu|Thr|Gly|Leu|Trp|Gln|Cys|Leu|Leu|Ser|Glu|Gly|Asp|
| | |335| | | | | |340| | | |345| | | |

```
GTG GCC CCT GAG ACA GGG CTG TGG CAG TGT CTA CTG AGT GAA GGT GAT       1158
Val Ala Pro Glu Thr Gly Leu Trp Gln Cys Leu Leu Ser Glu Gly Asp
        335                     340             345

AAG GTC AAG ATG GAC TCC AGG ATC CAG GTT TTA TCC AGA GGG GTG AAC       1206
Lys Val Lys Met Asp Ser Arg Ile Gln Val Leu Ser Arg Gly Val Asn
        350                 355                 360

CAG ACA GTG TTC CTG GCT TGC GTG CTG GGT GGC TCC TTC GGC TTT CTG       1254
Gln Thr Val Phe Leu Ala Cys Val Leu Gly Gly Ser Phe Gly Phe Leu
        365                 370                 375

GGT TTC CTT GGG CTC TGC ATC CTC TGC TGT GTC AGG TGC CGG CAC CAA       1302
Gly Phe Leu Gly Leu Cys Ile Leu Cys Cys Val Arg Cys Arg His Gln
380             385                 390                     395

CAG CGC CAG GCA GCA CGA ATG TCT CAG ATC AAG AGG CTC CTC AGT GAG       1350
Gln Arg Gln Ala Ala Arg Met Ser Gln Ile Lys Arg Leu Leu Ser Glu
                400             405                 410

AAG AAG ACC TGC CAG TGC CCC CAC CGG ATG CAG AAG AGC CAT AAT CTC       1398
Lys Lys Thr Cys Gln Cys Pro His Arg Met Gln Lys Ser His Asn Leu
            415             420             425

ATC   TGAGGCC                                                         1408
Ile
```

GENE ENCODING MUTANT L3T4 PROTEIN WHICH FACILITATES HIV INFECTION AND TRANSGENIC MOUSE EXPRESSING SUCH PROTEIN

This is a continuation of application Ser. No. 08/222,124, filed Apr. 4, 1994, now U.S. Pat. No. 5,620,881, which is a continuation of application Ser. No. 08/046,025, filed April 12, 1993, now abandoned, which is a continuation of application Ser. No. 07/746,701, filed on Aug. 16, 1991, now abandoned.

BACKGROUND OF THE INVENTION

The present invention relates generally to the manipulation of genetic materials and, more specifically, to recombinant procedures making possible the production of murine cell lines/strains or transgenic mice possessing desired characteristics.

CD4, expressed predominantly on the surface of human T helper cells, associates with the T cell receptor during T cell activation. In addition, CD4 binds to the gp120 envelope glycoprotein of HIV-1 which results in viral infection of CD4$^+$ cells. Murine L3T4, the counterpart of human CD4, shares 55% amino acid sequence homology with CD4 in their extracellular domains. However, L3T4 does not bind to gp120, rendering murine T helper cells resistant to HIV-1 infection. Interestingly, human CD4 transfected into murine cells binds HIV-1 on CD4$^+$ murine cells, but does not facilitate viral infection. The resistance to infection of CD4$^+$ murine cells is due to a defect in viral entry into the cell. The lack of affinity of gp120 for L3T4 and the inability of human CD4 to permit HIV-1 entry into CD4-transfected murine cells have thwarted efforts to develop a useful transgenic mouse model for HIV-1 infection.

The binding site of gp120 to CD4 has been mapped by site-directed mutagenesis of CD4 and analysis of mutant CD4 interactions with gp120. See, e.g., Clayton et al., Nature 335:363 [1988]. The crystal structure of CD4 confirmed that the critical region where CD4 attaches to gp120 is localized to an immunoglobulin-like domain in the C04 extracellular region. Residues 35–83 in domain I of CD4 are the primary contact location of gp120 with CD4. Some believe that amino acids in domain II of CD4 may also be important contact points for gp120 binding to CD4.

The critical region, however, for qp120 binding to CD4 resides between amino acids 43–55. The numbering for the CD4 and L3T4 amino acid sequences in this application is according to that of FIG. 3 in Littman et al., Nature 325:453 [1987]. (The numbering is based on L3T4 sequence in that reference.) Mutations introduced in this 13 amino acid span in human CD4 abrogate gp120 binding to the mutated CD4 receptors. Residues 44, 49, 51, 52, 57 and 64 are crucial for efficient gp120 binding to CD4. Residue 87 in CD4 is important for syncytium formation but does not play a role in gp120 binding, nor does it affect viral internalization. Mouse L3T4 and human CD4 are homologous at codons 58, 59, 64, 67 and 87.

SUMMARY OF THE INVENTION

In general, the invention, in one aspect, features a DNA sequence encoding a mutant L3T4 protein which, when expressed on the surface of a cell, is capable of facilitating infection of the cell by human immunodeficiency virus, e.g., HIV-1; the mutant protein includes at least one amino acid residue substitution or deletion in a first segment corresponding to positions 49–54 of a native L3T4 protein so as to increase homology between the first segment and its counterpart in a CD4 protein. For example, the first segment of the mutant protein is ProSerLysLeuAsn- (SEQ ID NO:1).

As noted above, the numbering for all amino acid sequences in this application is according to that of FIG. 3 in Littman et al., Nature 325:453 [1987]. The symbol "-" in an amino acid sequence stands for absence of a residue in that position.

By "infection", as used herein, is meant the occurrence of at least one of the sequential events following binding of gp120 to a L3T4 mutant: e.g., entry of virus into a host cell, reverse transcription of the viral RNA into DNA, integration of the viral DNA into the host cell's chromosome, synthesis of viral proteins, replication of the viral genome and release of virions from the host cells.

"Homology", as defined herein, refers to the degree to which the same or structurally similar amino acid residues (e.g., Leu and Ile) are found in a corresponding segment or position of both murine L3T4 protein and human CD4 protein.

In one preferred embodiment of the above-described DNA sequence, the mutant protein also includes at least one amino acid residue substitution or deletion in a second segment corresponding to positions 39–44 of a native L3T4 protein so as to increase homology betweea the second segment and its counterpart in a CD4 protein. For example, the second segment in the mutant protein is AsnGlnGly-SerPhe (SEQ ID NO:2).

More preferably, the mutant protein further includes at least one amino acid residue substitution or deletion in a third segment corresponding to positions 123–126 of a native L3T4 protein so as to increase homology between the third segment and its counterpart in a CD4 protein. For example, the third segment in the mutant protein is ProProGly-.

In an even more preferred embodiment, the mutant protein further includes at least one amino acid residue substitution or deletion in a fourth segment corresponding to positions 158–161 of a native L3T4 protein so as to increase homology between the fourth segment and its counterpart in a CD4 protein. As an example, the fourth segment of the mutant protein is GlyThrTrpThr (SEQ ID NO:3).

It is particularly preferable that the mutant protein further includes one amino acid substitution at position 57 of a native L3T4 protein so as to increase homology between amino acid residues at that position in the mutant protein and in a CD4 protein. For example, position 57 of the mutant protein is Ala.

Other preferred embodiments include a DNA sequence encoding a mutant L3T4 protein; the amino acid sequences of the mutant L3T4 protein corresponding to positions 1–38, 45–48, 58–122, 127–157, and 162–433 are identical to their counterparts in a native L3T4 protein and those corresponding to positions 39–44, 49–54, 123–126, and 158–161 are AsnGlnGly-SerPhe, ProSerLysLeuAsn-, ProProGly-, and GlyThrTrpThr, respectively.

In another aspect, the invention features a mammalian expression vector which includes any of the DNA sequences described above.

The invention also features a mammalian cell line or strain transfected with any of the DNA sequences described above. Preferably, such a cell line or strain is of murine origin.

Also within the invention is a process for transfecting mammalian cells with any of the DNA sequences described above.

Yet another embodiment of the invention is a transgenic rodent (e.g., a mouse, a rat, or a hamster) having cells which express a transgene containing any of the DNA sequences as described above. Preferably, in the transgenic rodent, expression of the transgene is activated by a cell-specific regulatory element, e.g., a CD3δ enhancer. It is also preferable that the transgenic rodent be a mouse.

Still within the invention is a process for introducing any of the DNA sequences described above into a rodent at an embryonic stage for establishment of a line of transgenic rodents which are suscepitible to infection by HIV-1 virus. Preferably, the rodent used in the process is a mouse. By "embryonic stage" is meant any point from the moment of conception (e.g., as where the sperm or egg bears the transgene) throughout all of the stages of embryonic development of the fetus, and preferably refers to a stage within the first eight days following conception.

The availability of a transgenic mouse model susceptible to HIV-1 infection should accelerate studies on the mode or modes of HIV-1 infection in vivo, and may result in the development of vaccines for HIV-1 infection or drugs for HIV-1-associated diseases.

Other features and advantages of the invention will be apparent from the following description of the preferred embodiments, and from the claims.

BRIEF DESCRIPTION OF THE DRAWINGS

The drawings are first described.

FIG. 1 is the DNA sequence of an L3T4 mutant according to this invention.

FIG. 2 is the DNA sequence of another L3T4 mutant according to this invention.

DETAILED DESCRIPTION OF THE PREFERRED EMBODIMENTS

Figure 3A:
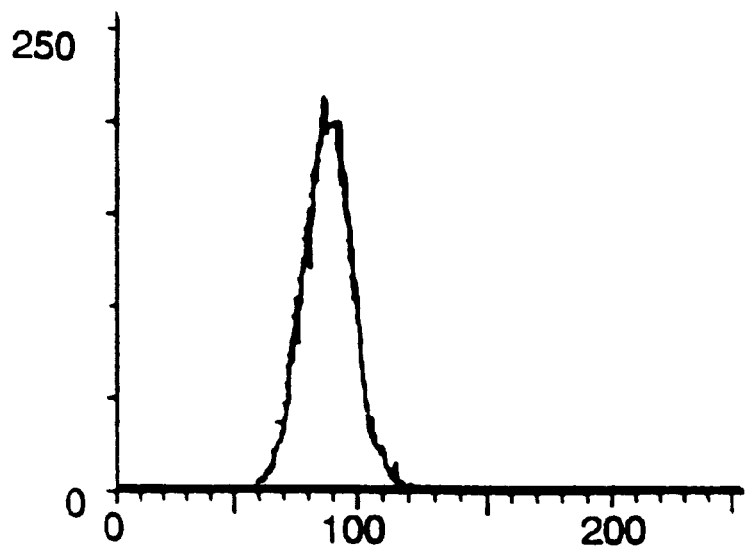
FIGS. 3A, 3B, 3C, 3D and 3E are graphs of results from fluorescence activated cell sorter analysis, showing gp120 binding to HeLa cells stably transfected with L3T4, M1, M5, M6 and CD4, respectively.

Several cell lines were or can be used in these studies; each cell line has characteristics which make it an appropriate model for testing the biological effects of mutant L3T4 receptors for HIV-1. All the cell lines described herein can be obtained from the American Type Culture Collection (ATCC) of Rockville, Md.

1. Cos-1 Cells (ATCC CRL 1650)

COS-1 cells are a monkey kidney cell line which is transformed by origin defective SV40.

2. EL-4 Cells (ATCC TIB 39)

EL-4 cells are a murine T lymphoma cell line which constitutively expresses wild type L3T4 and have the distinct advantage that they can be activated with lectins and phorbol esters.

3. NIH3T3 (ATCC CRL 1658)

NIH3T3 cells are a murine fibroblast cell line.

4. HeLa Cells (ATCC CCL 2)

HeLa cells are a human fibroblast-like cell line which can be used in the cell conjugation assay to measure class II MHC binding to L3T4 and L3T4 mutants.

5. Jurkat Cells (ATCC CRL 8163)

Jurkat cells are a human leukemia T cell line. Like EL-4 cells, they are subject to activation with lectins and phorbol esters to express IL-2. Jurkat cells can be used as a positive control in our HIV-1 infection studies, since human cells expressing CD4 are susceptible to HIV-1 infection.

6. CTLL-2 Cells (ATCC TIB 214)

CTLL-2 cells are a non-transformed murine cytotoxic T lymphocyte line which does not express L3T4 and is IL-2-dependent for cell growth. CTLL-2 cells can be induced into quiescence by culturing in IL-2-free media for 14 hours. HIV-1 infection studies can be conducted with CTLL-2 cells transfected with L3T4, CD4, L3T4 mutants during the period of quiescence and after stimulation with IL-2. These studies complement the EL-4 studies to determine if cell activation is required in murine cells for viral entry and replication.

7. BCL-1 Cells (ATCC TIB 197)

BCL-1 cells are a murine B cell line which expresses class II molecules on the cell surface and thus can be used in a cell conjugation assay to determine the ability of L3T4 mutants to bind with class II MHC.

8. RAJI Cells (ATCC CCL 86)

RAJI cells are a human EBV-infected B cell line and can be used as a control in the above-mentioned-cell conjugation assay, since murine L3T4 does not bind to human class II MHC proteins.

9. H-9/HTLV-IIIB Cells (ATCC CRKL 8543)

H-9/HTLV-IIIB cells are a human T cell line infected with HIV-1 which is used as a laboratory source of the virus.

I. Preparation and Selection of L3T4 Mutants

Site-Directed Mutagenesis of L3T4 and Molecular Cloning

Eight L3T4 mutants were constructed which mimic human CD4 in the CD4 gp120 binding region. The selection of mutations engineered into L3T4 was based on the identification of amino acids in CD4 which are required for binding to gp120. The mutants which we constructed range from a minimum of 4 amino acid substitutions and 1 deletion to 14 amino acid substitutions and 3 deletions.

The L3T4 mutants were constructed as follows. L3T4 was first prepared following the procedures set forth in Littman, et al, Nature 325:453–455 (1987). L3T4 cDNA with flanking Xba I restriction sites was cloned into M13mp18 (Amersham Corp., Arlington Heights, Ill.) at the Xba I site of the M13 bacteriophage. Correct orientation was determined by restriction enzyme analysis. Single-stranded DNA was isolated from phage supernatants. Site-directed mutagenesis of L3T4 was performed using a commercial kit (Amersham Corp., Arlington Heights, Ill.). The remaining steps in the construction of mutants are as described in the kit instructions.

Five oligonucleotides, designated as oligo 1 through oligo 5, respectively, were used to perform site-directed mutagenesis of L3T4. The sequences of the oligonucleotides and how they correspond to their counterparts in wild type L3T4 (i.e., numbers in parentheses) are shown in Table I.

TABLE I

| | | |
|---|---|---|
| Oligo 1 (247–294)[1]: | 5' GGAATCAAAACGATC---GTTCAACTTCGAAGGTCCTCTAATTAATAC* | (SEQ ID NO:4) |
| Oligo 2 (469–510): | 5' TGTCAAGGGGTTAGA---CCCAGGGGGGCTATCCAAGGTCAG | (SEQ ID NO:5) |
| Oligo 3 (577–612): | 5' GGTCACGGTGCAGGTCCAGGTGCCGCTGTCCTGAAC | (SEQ ID NO:6) |
| Oligo 4 (220–267): | 5' CGAAGGTCCTCTAATTAAGAAAGA---GCCTTGGTTCCCCAGAATCTT | (SEQ ID NO:7) |
| Oligo 5 (271–300): | 5' TTTTTTGGAATCAGCACGATC---GTTCAA | (SEQ ID NO:8) |

[1]All five oligonucleotides listed here are antisense primers used to construct the L3T4 mutations. The numbering for the DNA sequence is according to that of FIGS. 1 and 2 of this application.
*Where the mutants have a codon deletion (as indicated by dashes) the numbering scheme is maintained to simplify comparison to the wild type L3T4 sequence.

Shown in Table II are the scheme used in preparing the eight L3T4 mutants, which are designated as M1 through M8, respectively, and changes of amino acid residues in each L3T4 mutant.

TABLE II

| Mutant | Oligo Used | Amino Acids Changed in L3T4 |
|---|---|---|
| M1 | 1 | 49: Gly to Pro; 51: Pro to Lys; 52: Ser to Leu; 53: Gln to Asn; 54: delete Phe |
| M2 | 1 + 2 | All changes in M1; 123: Asn to Pro; 124: Ser to Pro; 125: Lys to Gly; 126: delete Val |
| M3 | 1 + 3 | All changes in M1; 158: Asp to Gly; 159: Phe to Thr; 161: Asn to Thr |
| M4 | 1 + 2 + 3 | All changes in M1, M2, M3 |
| M5 | 1 + 4 | All changes in M1; 39: Gln to Asn; 40: His to Gln; 42: delete Lys; 43: Gly to Ser; 44: Val to Phe |
| M6 | 1 + 2 + 3 + 4 | All changes in M1 to M5 |
| M7 | 1 + 4 + 5 | All changes in M5; 57: Phe to Ala |
| M8 | 1 through 5 | All changes in M6; 57: Phe to Ala |

FIGS. 1 and 2 show the nucleotide sequences of two L3T4 mutants, M1 and M8, respectively; also included are the amino acid sequences of the encoded proteins. Among the eight L3T4 mutants prepared, M1 contains minimal changes of amino acid residues from the wild type L3T4 and M8, on the other hand, contains maximal changes. Underlined amino acid residues denote differences between wild type and mutant L3T4 proteins (i.e., M1 or M8).

Subcloning, plasmid and phage purifications, ligations, etc. were performed according to standard molecular biological procedures. Maniatis, et al., Molecular Cloning, Cold Spring Harbor Laboratory, Cold Spring, N.Y., 1982. Mutations were screened by DNA sequencing using the dideoxy chain termination method. The cDNAs were cloned into the Xba I site of pRc/CMV (Invitrogen, Inc, San Diego, Calif.) for expression studies of L3T4, CD4, and the L3T4 mutants in stably transfected HeLa cells and NIH3T3 cells. The cDNAs were also cloned into the Xba I site of pCDM8 (Invitrogen, Inc., San Diego, Calif.) for transient expression studies in COS-1 cells. Expression of the cloned DNAs in both vectors is driven by the cytomegalovirus promoter; pRc/CMV also contains a neomycin resistance gene for G418 selection of stably transfected cells. The clones were screened for the correct orientation by restriction enzyme analysis. Plasmids were linearized by cutting with Sca 1 prior to electroporation for stable transfection into HeLa and NIH3T3 cells. More details regarding transfection are described below.

Gp120 Binding Studies
1. Murine Cells

Murine EL-4 cells were transfected with L3T4, CD4, and L3T4 mutants M1, M5, and M6 in a manner identical to that in which HeLa cells were transfected (see below). Bulk G418-resistant transfected EL-4 cells were tested for their ability to bind gp120. Two assays, radioligand binding assay and fluorescence activated cell sorter ("FACS") analysis, were used to measure gp120 binding to EL-4 cells.

In the radioligand binding assay, $^{125}$I-gp120 was used to react with $3 \times 10^6$ transfected EL-4 cells for 2 hours at 4° C. The transfected EL-4 cells were then centrifuged through a silicon/paraffin oil layer and counted in a gamma counter. As the number of mutations in L3T4 increases and L3T4 becomes more CD4-like in the gp120 binding region, the affinity of EL-4 transformants for $^{125}$I-gp120 improved (Table III, middle column).

TABLE III

| EL-4 Transfectant | $^{125}$I-gp120 Bound (CPM) | Gp120+Cells by FACS (%) |
|---|---|---|
| EL-4 control | 100 | 5 (10% L3T4+) |
| L3T4 | 93 | — |
| M1 | 4992 | 6 |
| M5 | 6818 | 25 |
| M6 | 12,631 | 14 |
| CD4 | 28,258 | 7 (9% CD4+ cells) |

Gp120 binding to EL-4 transfectants was also measured by the FACS analysis. More specifically, the EL-4 transfectants were reacted with 80 nM gp120 (Genentech, Inc., San Francisco, Calif.; or prepared following procedures described in Lasky et al., Cell 50:975 [1987]) in sterile phosphate buffered saline ("PBS") for 2 hours at 23° C. The cells were then washed twice with cold PBS followed by reaction with mouse anti-gp120 (New England Nuclear, Boston, Mass.) for 30 minutes at 4° C., two washes with cold PBS, and staining with FITC-labelled goat anti-mouse IgG for 30 minutes followed by two washes with PBS. The data (Table III, right-hand column) indicate that gp120 bound to EL-4 cells transfected with L3T4 mutants M5 and M6. Gp120 on transfected EL-4 cells was detected by anti-gp120 and FITC-labeled goat anti-mouse IgG. However, the low level of cells bound to CD4-transfected cells is reflected by the low level of cell surface expressed CD4. All EL-4 transfected cells studies in these preliminary studies were from bulk G418-resistant cultures. Thus, subcloning of transfectants prior to HIV-1 infection studies was required in order to isolate clones expressing high levels of the transfected gene.

2. Monkey and Human Cells

CD4, L3T4, and L3T4 mutants M1, M5, and M6 were stably transfected into HeLa cells and transiently transfected into Cos-1 cells as follows.

HeLa cells were stably transfected with L3T4, CD4, and mutant L3T4-containing plasmids by electroporating $2\times10^6$ trypsinized cells in 0.5 ml of cold phosphate-buffered saline containing 20 ug of the SCA 1 digested linearized plasmid at 200 V and 500 uFD. After the transfection, the cells were placed in the culture media. Two days later the transfected cells were selected by addition of 600 ug/ml Geneticin (G418). Dead cells were removed after 3 days and the remaining live cells were cultured for another 1–2 weeks. Subclones were cultured and screened for cell surface expression of the transfected gene. These cells were grown in media containing a maintenance dose of G418 (100 ug/ml).

COS-1 cells were transiently transfected by the DEAE method of Seed et al., Proc. Natl. Acad. Sci. USA 84:3365 [1987]). Briefly, COS-1 cells were platedon 100 mm tissue culture plates at 40–60% confluence 24 hours prior to the transfection. The cells were then washed and placed in 3 ml RPMI containing 10% NuSerum (Collaborative Research, Inc., Bedford, Mass.) followed by addition of 0.33 ml of a 4 mg/ml solution of DEAE dextran, 3.5 ul of 100 mM chloroquine, and 15 ug of plasmid. The cells were incubated for 3 hours followed by removal of the media and incubation with 3 ml of PBS containing 10% DMSO for 1 minute. The cells were washed twice with PBS and incubated in culture media for 2 days prior to HIV-1 infection studies.

The presence of cell surface expressed L3T4, L3T4 mutants, and CD4 was verified by FACS analysis using anti-CD4 and anti-L3T4 (Bectin-Dickinson, Mountain View, Calif.). More specifically, transfected G418-resistant cells were removed from the petri dishes by incubation with cold PBS containing EDTA and gentle scrapping with a sterile plastic policeman. The cells were then reacted with anti-CD4 on anti-L3T4 (GK1.5) at 4° C. for 30 minutes. The CD4, L3T4, and mutant L3T4 transfected cells were washed twice with PBS, and reacted with FITC-labelled goat anti-mouse IgG or goat anti-rat IgG, respectively, and sorted on a cell sorter for analysis of cell surface expression of CD4 and L3T4. The mutations in the second domain of L3T4 at amino acids 123, 124, 125, and 126, and 158, 159 and 161 partially abrogated the anti-L3T4 binding epitope of the GK1.5 monoclonal antibody.

Figure 3B:
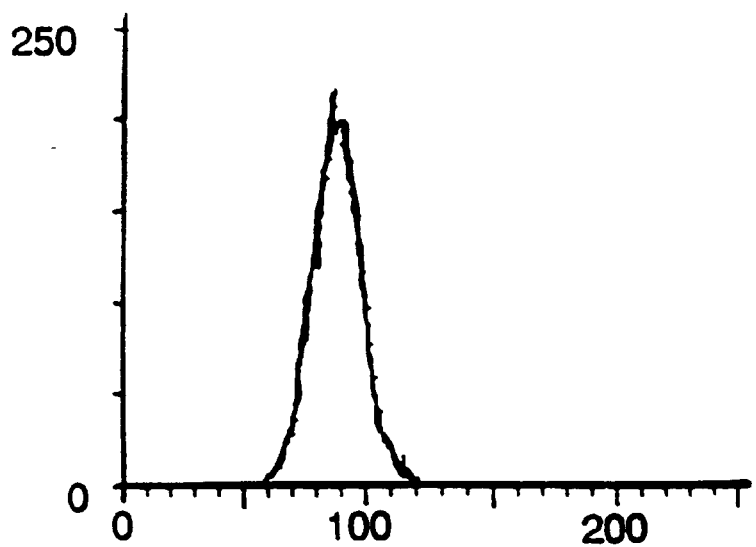
Figure 3C:
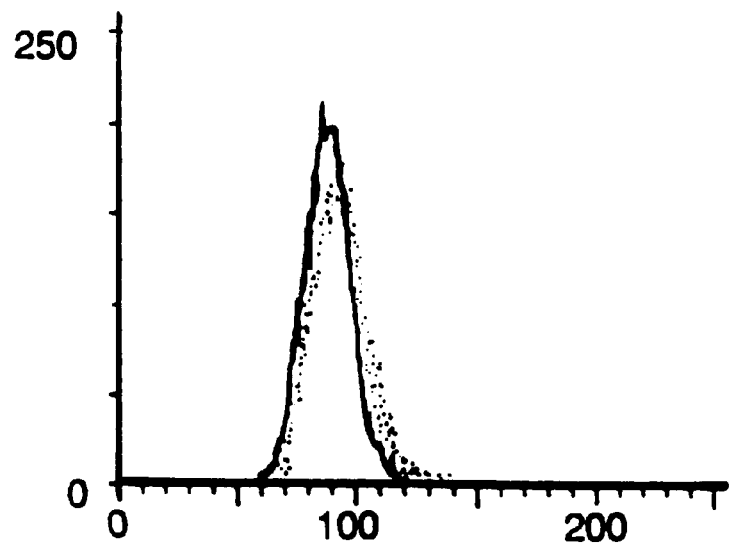
Figure 3D:
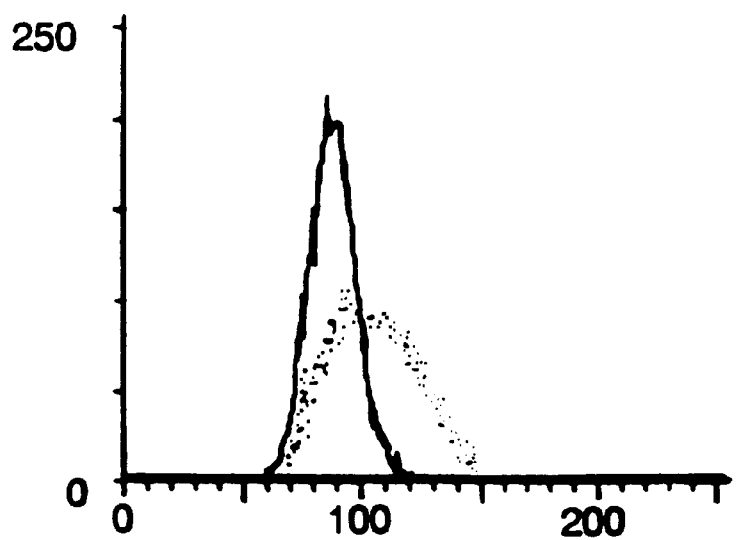
Figure 3E:
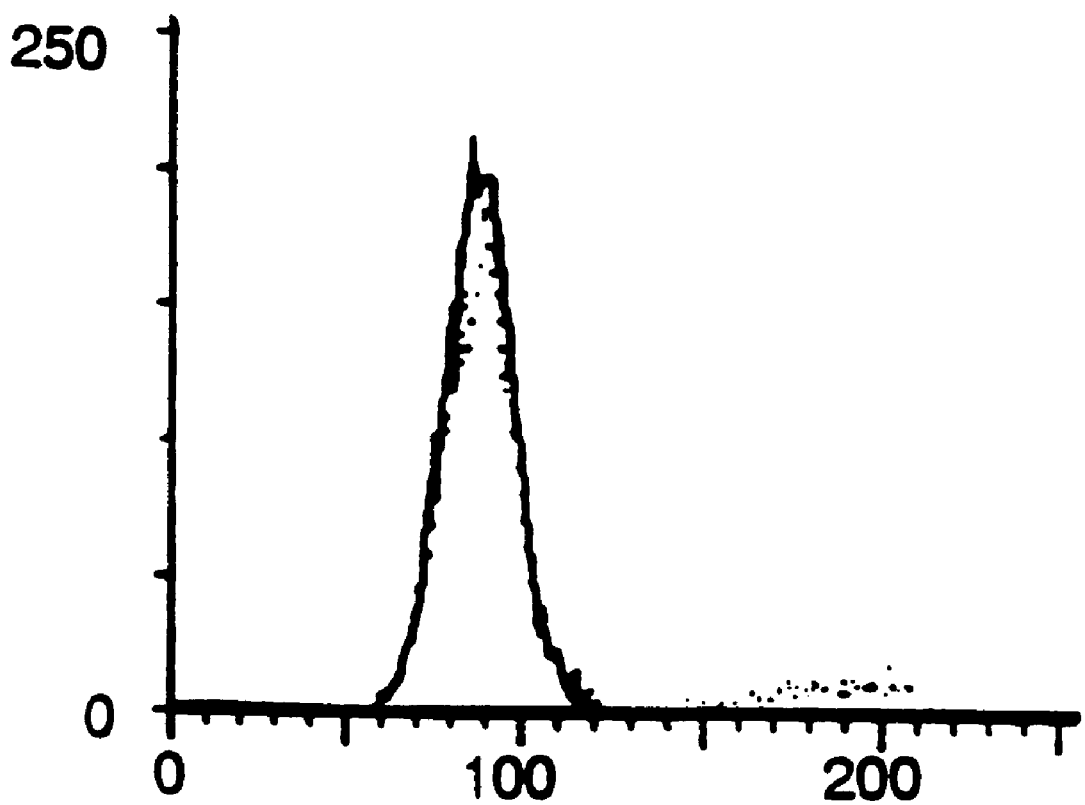

FACS analysis of transfected HeLa cells reacted with gp120, anti-gp120, and recognition by FITC labelled goat anti-mouse IgG show that L3T4 did not bind gp120 (FIG. 3A), while cell surface expressed CD4 bound gp120 (FIG. 3E). L3T4 mutants M1, M5, and M6 bound gp120 increasingly better as more mutations were engineered into L3T4 (FIGS. 3B–3D). Both COS-1 cells and HeLa cells transfected with mutants M1, M5 and M6 exhibited similar gp120 binding patterns. CD4+ cells clearly bound more gp120 as evidenced by the increased florescence level over M6 transfected cells. The number of HeLa cells expressing CD4, however, was low. These results show that L3T4 can bind gp120 by reconstruction of a CD4-like gp120 domain. Furthermore, gp120 binding to a L3T4 mutant could be detected, albeit at a very low level, by incorporating into L3T4 as few as 4 amino acid substitutions and 1 deletion at L3T4 codons 49, 51, 52, 53, and 54, respectively (i.e., M1). The change of glycine 49 in L3T4 to a proline residue may induce a large structural change which plays a major role in gp120 binding in CD4. Prolines cause abrupt structural changes in the protein backbone. By increasing the number of mutations in L3T4 to CD4 residues, more gp120 binding was observed. This supports the view that the nature of CD4 residues crucial for gp120 binding is additive.

3. Determination of gp120 Dissociation Constants

Transfected and subcloned cells are used to determine the gp120 dissociation constant (Kd) for the L3T4 mutants by Scatchard analysis. Measurement of the affinity of the mutant L3T4 receptors for gp120 provides important information about the potential for these mutants to facilitate HIV-1 infection. These data also provide information about the quantitative importance of each set of mutations engineered into L3T4. The gp120 binding data are thus one of the criteria for selecting an L3T4 mutant for development of a transgenic mouse.

Cell sorted and subcloned transfectants are used in whole cell saturation binding analysis to calculate the affinity of gp120 for cell surface-expressed L3T4, CD4, and L3T4 mutants. Gp120 is radioiodinated by the lactoperoxidase/ glucose oxidase method using a commercially available kit (Bio Rad Laboratories, Richmond, Calif.). Binding studies of $^{125}$I-gp120 to stably transfected CTLL-2 cells are performed in RPMI-1640 median containing 1%, BSA at $5\times10^6$ cells/0.1 ml for 2 hours at 22° C. The cold gp120 concentration in the binding reaction range from 0.5 uM to 1 nM with the $^{125}$I-gp120 added at $5\times10^5$ CPM per sample. The cells are then pelleted by centrifugation through a silicone/ paraffin oil layer to separate the cells with bound $^{125}$I-gp120 from the free ligand. $^{125}$I-gp120 bound to the cells is measured in a gamma counter to determine the affinity of mutant L3T4 receptors for gp120.

HIV-1 Infection Studies

Results from infection studies with transfected cells expressing various L3T4 mutants form the basis for selecting a mutant L3T4 gene for developing a transgenic mouse model. The cell activation studies with two murine cell lines, EL-4 and CTLL-2 cells, provide important information concerning the need to stimulate murine cells to allow HIV-1 entry or replication. Also, the experiments with CTLL-2 cells may be desirable, since this cell line approximates normal lymphoid cells more than EL-4 cells, a T cell lymphoma cell line.

1. Entry of HIV-1 into cells expressing L3T4 mutants

Human CD4 transfected into NIH3T3 cells was shown to bind HIV-1 but viral entry into the cell did not occur (Maddon et al., Cell 47:333 [1986]). We used the polymerase chain reaction ("PCR") to determine if the L3T4 mutants could act to bind to gp120 and facilitate entry of HIV-1 into COS-1 cells and NIH3T3 cells.

(a) COS-1 Cells

COS-1 cells, a monkey cell line, mere transfected with L3T4, CD4, an L3T4 mutants M1, M5 and M6, which were cloned into pCDM8, a vector designed for high level transient expression in cell lines harboring origin-defective SV40. Transiently transfected COS-1 cells were infected with HIV-1/IIIB. All procedures followed the standard practices outlined by the NIH for the handling of infectious retroviruses. Cells transfected with L3T4, CD4 and L3T4 mutants were tested for their susceptibility to HIV-1 infection. HIV-1/IIIB-titered supernatants were added to $3\times10^5$ transfected cells for 2–4 hours at a multiplicity of infection ("moi") of 0.1. Following the infection the cells were washed 3 times with media and cultured for 2 days. The cells were then harvested by trypsinizing from the plate and subjected to PCR analysis to determine the presence of HIV-1 gag RNA and DNA.

Cellular RNA and DNA were isolated herein by first lysing the pelleted cells in a buffer containing 25 mM Tris-HCl, pH 7.5, 0.5 mM EDTA and 0.5% NP40. Vanadyl ribonucleoside complex was added to the lysis buffer to inhibit ribonuclease activity. The cell lysate was then centrifuged and the supernatant containing the RNA was treated with 500 ug/ml proteinase K and 1% SDS for 30 minutes followed by phenol extraction and isopropanol precipitation. The RNA was treated with RAase-free DNAase to remove residual viral DNA which might originate from lysed cells in the viral stock. The RNA was then converted to cDNA by MMLV reverse transcriptase as recommended by the supplier (BRL, Inc., Gaithersburg, Md.) using oligo d(T) as the primer, followed by analysis of gag by PCR using HIV-1 gag sense and antisense primers (Schnittman et al., Science 245:305 [1989]). The pelleted nuclear material from the NP40 cell lysis was reconstituted in 200 ul of lysis buffer containing proteinase K, incubated for 1 hour at 55° C., then at 96° C. for 15 minutes. Aliquots of the cDNA reaction and the nuclear material were used directly for PCR analysis.

PCR Analysis was performed as follows. We used as primers a sense sequence sk38 (Id.) and a second antisense sequence (positions No. 1421–1449), which define a 310 base pair gag sequence. DNA samples were heated at 95° C. prior to addition to the PCR. All PCRs described herein were performed using master PCR mixes which art aliquoted and kept at −20° C. Taq polymerase (Perkin Elmer) is added to the PCR mix prior to the PCR reaction. The PCR conditions were as follows: denaturation at 95° C. for 1 minute, annealing at 55° C. for 1 minute, and extension at 72° C. for 30 seconds for 30–35 cycles. PCR products were separated by agarose gel electrophoresis, Southern blotted, and hybridized to nick translated [$^{32}$P]-dCTP-labelled gag or tat DNA probes.

Hybridization and prehybridization were conducted as follows. Filters were washed and UV cross-linked to immobilize the RNA and prehybridized at 42° C. for 5 hours in a solution containing 50% formamide, 5×SSC, 25 mM sodium phosphate, pH 6.5, 0.1% SDS, 5×Denhardt's and 100 ug/ml denatured salmon sperm DNA. DNA probes were labelled by nick translation using a nick translation kit (Bethesda Research Labs, Inc., Gaithersburg, Md.) and [$^{32}$P]-dCTP as a radioactive label. Hybridization conditions were similar to the prehybridizing conditions except the solution is 2×Denhardt's dextran sulfate is added to a final concentration of 8%, and the hybridization proceeds for 20 hours. Following hybridization, filters were washed twice at room temperature in 2×SSC/0.1% SDS for 10 minutes, and twice at 59° C. for 20 minutes each in 0.2×SSC/0.1% SDS. The filters were dried and placed against Kodak XAR film with an intensifying screen.

Figure 4A:
FIGS. 4A and 4B are autoradiographs of agarose gel electrophoresis, showing the presence of HIV-1 gag DNA and RNA, respectively, in COS-1 cells transfected with various L3T4 mutants of the invention or CD4 following HIV-1 infection.
Figure 4B:

Southern blot analysis show that mutant L3T4-transfected and CD4-transfected COS-1 cells contain gag RNA (FIG. 4A) and DNA (FIG. 4B). Non-transfected COS-1 cells, mock-transfected COS-1 cells, and L3T4-transfected COS-1 cells did not show the presence of gag by PCR analysis. These data provide evidence that mutations designed into L3T4 to construct a gp120 binding domain may facilitate HIV-1 binding and internalization. The data also correlate to those from the FACS analysis for gp120 binding (FIGS. 3A–3E), i.e., the increased level of gp120 binding to the L3T4 mutants is reflected by the level of HIV-1 gag PCR products. As a quantitative control, we verified the presence and quantity of cDNAs and genomic DNA for β-actin by PCR analysis (data not shown).

(b) NIH3T3 Cells

We further demonstrated that L3T4 mutant M6 could facilitate HIV-1 infection in a murine cell line NIH3T3 cells. L3T4, CD4, and L3T4 mutant M6 were cloned into pRc/ CKV and stably transfected into NIH3T3 cells in a manner described above. NIH3T3 transfectants were then incubated with HIV-1/III-B for 4 hours at an moi of 0.2. The cells were washed, cultured for 2–7 days prior to analysis for viral internalization and replication. During the post-infection culture period, the cells were passed by treatment with trypsin to remove the cells from the tissue culture plate on the first day after HIV-1 infection and then every 3 days. Trypsin treatment also destroyed any residual virus in the culture. The cells were tested for the presence of internalized HIV-1 by PCR amplification and southern blotting. For PCR analysis, HIV-1 gag RNA and DNA were identified by using the above-mentioned oligonucleotides that specify a 310 base pair DNA.

Figure 5A:
FIGS. 5A and 5B are autoradiographs of agarose gel electrophoresis, showing the presence of HIV-1 gag DNA and RNA, respectively, in NIH3T3 cells transfected with an L3T4 mutant of the invention following HIV-1 infection.
Figure 5B:
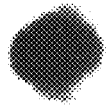

Results of Southern blotting for HIV-1 gag RNA, which was converted to cDNA with reverse transcriptase (FIG. 5A), and nuclear DNA (FIG. 5B), show that mutant M6 facilitated entry of HIV-1 into NIH3T3 cells. More specifically, the data indicate the presence of a 310 base pair DNA in M6 transfected cells amplified with oligonucleotides specifying the gag gene of HIV-1. Thus, L3T4 mutant M6, when expressed on the surface of transfected murine cells, can bind HIV-1 and allow viral entry into the cells.

2. Production of Spliced HIV-1 Tat RNA in L3T4-Mutant Transfected NIH3T3 Cells Infected with HIV-1.

Tat is a 15 kD transactivator protein of HIV-1 which activates the viral LTR, driving viral replication. The presence of spliced tat RNA is a reliable indicator of HIV-1 infection and replication. Tat RNA is generated by splicing RNA segments from several distant locations within the virion genome during viral replication. Tat RNA splicing initially occurs during low level viral transcription. Production of the tat protein ensues which further activates the viral LTR to amplify HIV-1 replication.

PCR amplification was employed to detect spliced HIV-1 tat RNA in NIH3T3 cells transfected with L3T4, CD4, and L3T4 mutant M6. The PCR fragment was designed to detect a 240 base pair DNA using as primers two sequences, i.e., a sense sequence (5411–5434) and an antisense sequence (7978–8001), which are separated by 2600 base pairs within the HIV-1 genome. We performed Southern blot analysis of tat RNA (converted to cDNA, using oligo d(T) as the primer) from HIV-1 infected NIH3T3 cells which were transfected with L3T4, CD4 and the L3T4 mutant M6. We tested transfected NIH3T3 cells for the presence of tat transcripts.

Figure 6:
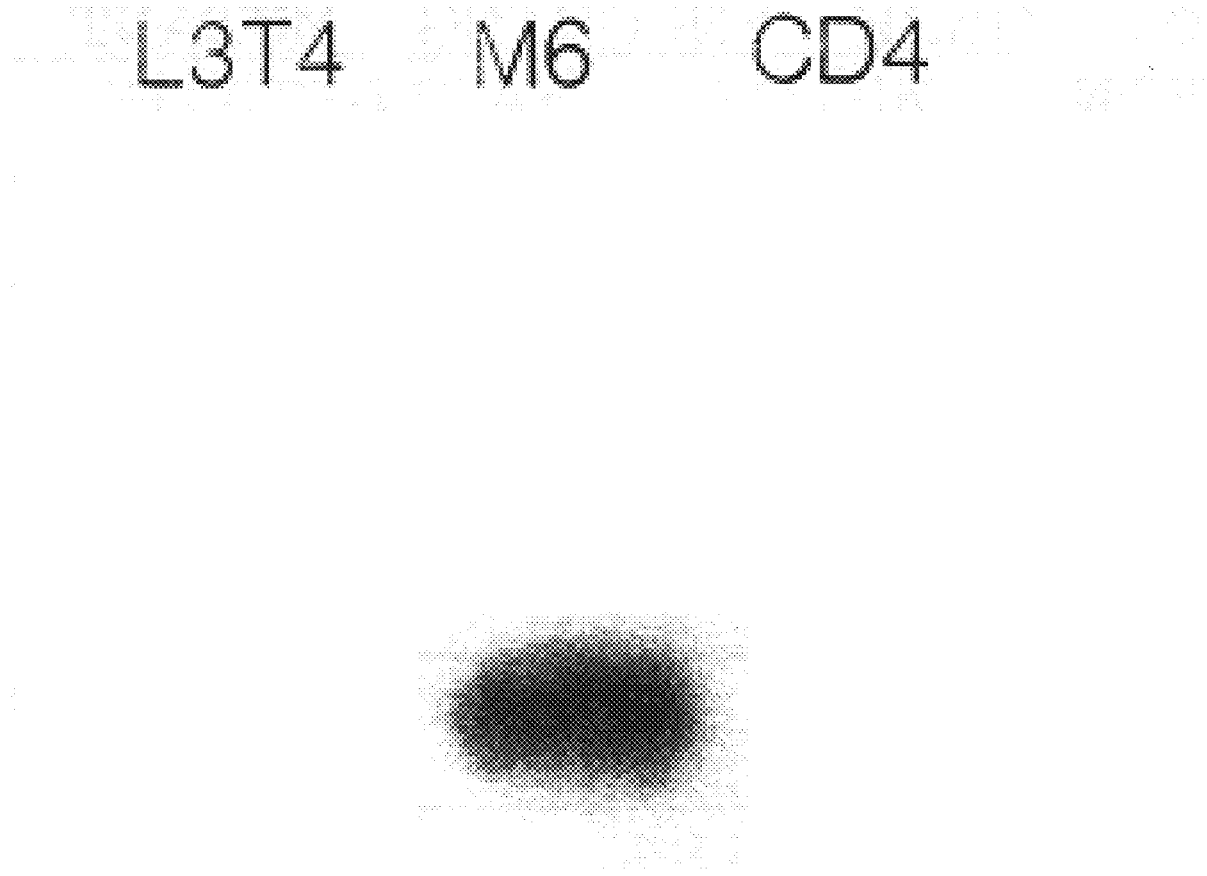
FIG. 6 is an autoradiograph of agarose gel electrophoresis, showing the presence of HIV-1 tat RNA, in NIH3T3 cells transfected with an L3T4 mutant of the invention following HIV-1 infection.

Southern blot analysis shows L3T4 mutant M6 facilitates entry and replication of HIV-1 as evidenced by the presence of the 240 base pair spliced tat CDNA fragment; CD4 and L3T4 transfected cells were negative for tat cDNA (FIG. 6).

3. Measurement of HIV-1 p24 Gag Antigen and Reverse Transcriptase Activity

We performed infection studies with HeLa cells transfected with L3T4, L3T4 mutant M6, and CD4. HeLa cells were transfected following a procedure similar to that for transfecting NIH3T3 cells as described above. 2×10$^5$ transfected HeLa cells plated on 60 mm plates in 1.5 ml of media were then infected with HIV-1/IIIB at an moi of 0.1 for 2 hours. The cells were washed twice with media, cultured overnight, and trypsinized the following day to destroy any remaining virus. Three days later the cells were removed by trypsin and split 1:5. On day 6 after the infection, culture supernatant was removed for analysis of HIV-1 p24 gag antigen by a commercial ELISA kit (New England Nuclear, Boston, Mass.). The results show that HIV-1 p24 antigen was present in the supernatant of N6- and CD4-transfected HeLa cells while L3T4-transfected cells only exhibited background levels of p24 antigen (Table IV, Experiments 1, 2 and 3). In other words, M6 transfected cells were demonstrated to be capable of producing a viral protein, which is an essential feature of infection.

Note that M1 causes a consistent but marginal increase in gp120 binding as observed by FACS analysis in both HeLa cells (FIG. 3B) and COS-1 cells (data not shown). As shown in Table III, results from $^{125}$I-gp120 binding studies also indicate that M1 transfected EL-4 cells bind gp120, but less efficiently than M5, M6, and CD4. The PCR analysis shows clearly that the virus can enter via the M1 receptor (FIGS. 4A and 4B). However, only very low levels of p24 gag were observed in infection experiments with M1-transfected HeLa cells. Apparently, PCR analysis can greatly amplify HIV DNA from M1 infections to simulate the data of M5, M6 and CD4 infections. On the other hand, insufficient virus may enter through M1 to enable us to observe increased p24 gag from viral replication under the conditions of our infection studies, since M1 is less efficient than M5, M6, and CD4 for binding gp120.

TABLE IV

| Experiment No. | HeLa cell Transfectant | gag p24 (pg/ml) |
|---|---|---|
| 1 | L3T4 | 7 |
|   | M6 | 125 |
|   | CD4 | 145 |
| 2 | HeLa | 16 |
|   | L3T4 | 10 |
|   | M6 | 355 |
|   | CD4 | 463 |
| 3 | HeLa | 3 |
|   | L3T4 | 7 |
|   | M5 | 472 |
|   | M6 | 350 |
|   | CD4 | 459 |
| 4 | HeLa | 113 |
|   | M6 | >578 |
|   | CD4 | >578 |

We further demonstrated that transfected HeLa cells are susceptible to CD4-independent HIV-1 infection as reported by Page et al., J. Virol 64:5270 [1990]. HeLa cell transfectants were infected with HIV-1/IIIB at an moi of 0.2 for 14 hours (Table IV, Experiment 4). The cells were then treated as described above except that the HeLa cells in Experiment 4 were cultured for 14 days. The p24 levels in the culture supernatant above 30 are positive for HIV according to the supplier of the ELISA HIV assay kit (New England, Boston, Mass.). When a longer HIV-1 incubation time was employed, non-transfected HeLa cells exhibited modest levels of p24 antigen (Table IV, Experiment 4). These results clearly show that HeLa cells transfected with L3T4 mutants, such as M6, can undergo a mode of HIV-1 infection through the mutant L3T4 receptor.

Reverse transcriptase is another protein expressed by HIV-1 and thus can also serve as a criterion of viral infection. Reverse transcriptase activity in the supernatant of transfectant cell culture infected by HIV-1 is measured following the procedure described in Poiesz et al., Proc. Natl. Acad. Sci. USA 77:741 [1980].

4. Cell Activation Studies With Murine Cell Lines

Two murine cell lines, EL-4 and CTLL-2 cells, are used to determine if cell activation is required for viral entry and replication in murine cells transfected with L3T4, CD4, L3T4 mutants. Jurkat cells, a human cell line expressing CD4 and susceptible to HIV-1 infection, are used as a positive control.

Jurkat and EL-4 cells are stimulated by incubation in the presence or absence of phytohemagglutinin ("PHA", 5 ug/ml) and phorbol myristic acid ("PHA", 5 ng/ml), both from Sigma, St. Louis, Mo., 24 hours prior to HIV-1 infection. After the infection, stimulated cells are washed 3 times with media and placed in culture for several days. The cells are then processed for PCR analysis, and the culture supernatants analyzed for p24 antigen and reverse transcriptase activity. CTLL-2 cells, which are IL-2-dependent for cell growth, are maintained in media containing 10 U/ml of IL-2 or placed in IL-2-deficient media 14 hours prior to addition of HIV-1. After the infection, the cells are washed 3 times and cultured in the presence of IL-2 for several days.

To verify that Jurkat and EL-4 cells are activated by PHA/PMA treatment, we perform a Northern blot analysis to detect increased levels of IL-2 mRNA. CTLL-2 cell activation by IL-2, on the other hand, is verifiable by cell growth, i.e., CTLL-2 cells will die if they fail to respond to IL-2.

Class II MHC Interaction

L3T4 and CD4 interact with nonpolymorphic determinants of murine and human class II MHC, respectively. This interaction facilitates association with the T cell receptor resulting in signal transduction. These events are important for efficient recognition of antigen by the T cell receptor. Because L3T4 plays a role in immune responses, it is preferred that an analysis of L3T4 mutants be performed to determine how an L3T4 mutant used to establish a transgenic mouse line may affect class II binding.

The need to preserve class II MHC binding affinity for L3T4 mutants depends on whether preservation of class II MHC binding ability by L3T4 mutants is an advantage. In any event, L3T4 mutants which bind gp120 but differ in their capability to bind class II molecules may be useful tools for future in vivo studies with transgenic mice.

HeLa cells transfected with L3T4, CD4, and L3T4 mutants are used to analyze the binding to a murine B cell line BCL1, which expresses class II moleculles on the cell surface. We use a cell conjugation assay to determine the ability of L3T4 mutants to bind with class II MHC determinants. This assay was used to measure the effect of mutations within CD4 on interaction with human class II MHC. See Clayton et al., Nature 339:548 [1989]. The cell conjugation assay involves the visual and radioisotope measurement of L3T4 or mutant L3T4-transfected HeLa cells conjugated with the murine B cell line. The conjugation assay is performed as described by Clayton et al. Id. Briefly, $10^8$ BCL1 cells is labelled with 0.5 mCi of $^{51}$Cr for 2 hours at 37° C. and washed three times. Radioactively labelled B cells ($10^7$) are incubated with L3T4-transfected, L3T4 mutant-transfected, or vector alone-transfected HeLa cells grown to 80% confluence in 6 well microtiter plates for 1 hour at 37° C. Unbound B cells are removed from the plate by several washes. The bound cells, on the other hand, are lysed with 1% Triton in PBS and the supernatant is collected and counted. This experiment is also performed without labelling the B cells; conjugation is scored by viewing the bound cells by light microscopy.

The specificity of the interaction is checked by the following controls: 1) pretreatment of the B cells with anti-murine class II MHC (Accurate Chemical Corp., Westbury, N.Y.); 2) treatment of the transfected HeLa cells with anti-L3T4, except for M6 and M8 where other anti-L3T4 antibodies are tested); and 3) interaction of RAJI cells, a human EBV-infected B cell line; as discussed above, murine L3T4 does not bind to human class II MHC proteins.

Syncytium Assay

Syncytia formation is the cell to cell fusion which forms multinucleated giant cells and is observed in AIDS (acquired immunodeficiency syndrome) patients. Syncytia results from the interaction of cell surface viral gp120 with a gp120 receptor, e.g., CD4, on another cell. Syncytia formation is a reliable indicator of HIV-i infection and the presence of gp120-binding proteins which facilitate cell to cell fusion. In analogous to assays for human syncytia formation, we measure syncytia in L3T4-mutant transfected murine lymphocytic CTLL-2 cells following the method set forth below.

$3 \times 10^5$ L3T4, CD4, or mutant L3T4-transfected CTLL-2 cells are plated in 10 mm microtiter wells. $1 \times 10^5$ H-9/HTLV-IIIB cells which are chronically infected with HIV-1/IIIB are added to the wells containing transfected CTLL-2 cells. The cocultivation assays are then incubated 24–72 hours at 37° C. Thereafter, the wells are scored for syncytia formation.

II. Establishment of A Transgenic Mouse Line Susceptible to HIV-1 Infection

Construction of a L3T4 Mutant Transgene

1. Selection of an L3T4 Mutant

One L3T4 mutant is selected for development of a transgenic mouse. The criteria for selection of a candidate L3T4 mutant are based on the following data generated from the studies described above.

(a) Affinity for recombinant gp120, as determined by Scatchard analysis of gp120 for L3T4 mutant-transfected CTLL-2 cells.

(b) Ability of the L3T4 mutants to facilitate HIV-1 infection.

(c) Ability of L3T4-mutant transfected cells to fuse with HIV-1-infected H9 cells.

(d) Preservation of MHC class II interactions. This criteria is not essential where wild type L3T4 are still expressed. Preservation of class II MHC binding is considered a negative factor in the selection of a candidate L3T4 mutant where expression of wild type L3T4 is unaffected in EL-4 cells.

2. Construction of an L3T4 Mutant Transgene with the CD3δ Enhancer-Promoter

Figure 7A:
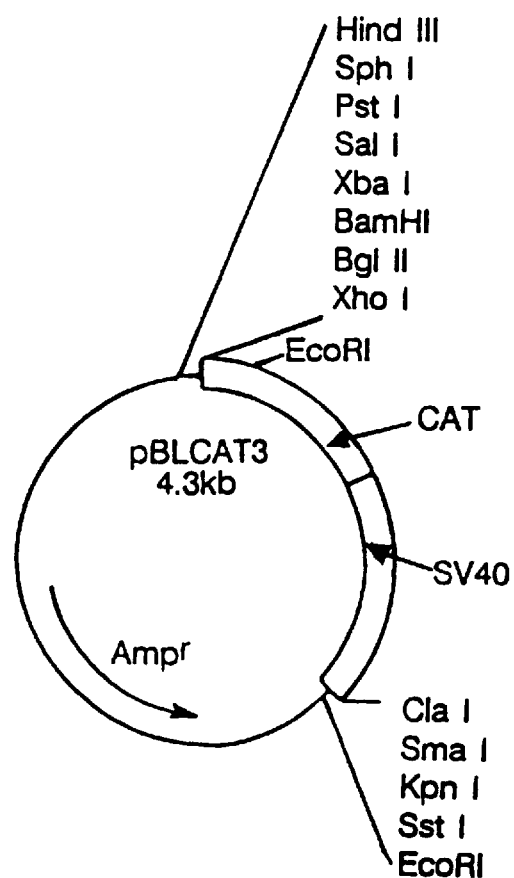
FIG. 7A is a representation of a vector, pBLCAT3, used in preparing a DNA construct in the generation of a L3T4 mutant transgenic line.

An L3T4 mutant is inserted into pBLCAT3 (FIG. 7A, Luckow et al., Nuc. Acid Res. 15:5491 [1987] containing the murine CD3δ enhancer/promoter, which can be prepared following Georgopoulos et al., EMBO 7:2401[1988], for tissue-specific expression of the L3T4 mutant in the transgenic mouse model. CD3δ promoter is inserted into the Xba I site and CD3δ0 enhancer into the Sma I site of pBLCAT3. The CD3δ enhancer exhibits tight tissue-specific expression in T cells, while the promoter was not T cell specific. It is preferred to generate enhanced expression of mutant L3T4 in T cells in the transgenic mouse model. Expression of mutant L3T4 in T lymphocytes best approximates the human system where $CD4^+$ T cells are a main target for HIV-1 infection.

Figure 7B:
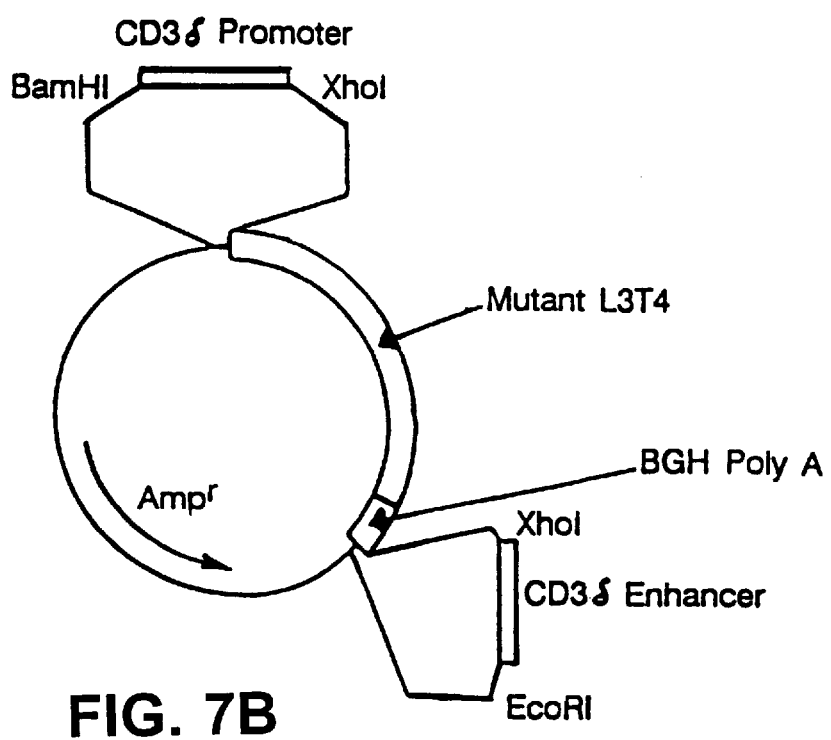
FIG. 7B is a representation of such a DNA construct.

An L3T4 mutant cDNA, e.g., M6, is first excised from pRc/CMV with Xba I and blunt ended with T4 DNA polymerase. The L3T4 mutant is then cloned into the Xho I-Sma I site of CD3δ enhancer/promoter-containing pBLCAT3, which is also blunt ended with T4 polymerase. The L3T4 mutant replaces the CAT gene between these restriction sites and is situated immediately 3' to the CD3δ promoter and 5' to the CD3δ enhancer (FIG. 7B). Enhancers are known to function independently of their orientation; however, the CD3δ enhancer is more efficient when it is situated 3' to the CD3 gene. Id. Prior to microinjection into eggs, the DNA is made linear by cutting with Sph I. All DNA manipulations are as described in Maniatis et al., Molecular Cloning. Cold Spring Harbor Laboratory, Cold Spring, N.Y., 1982.

Development and Breeding Founder Transgenic Mice

The best readout for testing the HIV-1 infectivity of mutant L3T4+ cells is in live animals or live animal tissue expressing these genes. Founder transgenic mice are developed and bred to establish a transgenic mouse colony.

1. Developing Founder Mice

The transgene constructed in a manner as described above is injected into female $F_2$ hybrid zygotes [(C57B1/6J×CBA/J)$F_1$ female× (C57B1/6J×CBA/J)$F_1$ male]. The generation and breeding of transgenic mice, is more efficient when $F_2$ zygotes are used for microinjection. Brinster et al., Proc. Natl. Acad. Sci. USA 82:4438 [1985]. The microinjected eggs are then implanted into pseudopregnant C57B1/6J female mice to serve as foster mothers for the founder mice. The presence of the transgene in the founder mice is determined by methods as described below.

2. Breeding Founder Mice

Founder mice are bred according to standard methods for breeding laboratory mice and screened for the presence of the injected transgene by performing a PCR analysis and a genomic DNA Southern blot analysis from a tail biopsy as described below. Those bearing the L3T4 mutant are mated with $F_1$ (C57B1/6J×CBA/J) male or female mice, depending on the sex of the mutant L3T4-bearing founder mice. We breed heterozygous transgenic mouse population and approximately one-quarter of the heterozygous intercrosses are homozygous for the mutant L3T4 gene. Where the integrated DNA produces a recessive lethal effect, the heterozygous transgenic mice are used as the sole source of tissue for HIV-1 infection studies. Homozygosity are confirmed by outcrossing the presumptive homozygous mice to a nontransgenic mouse, to confirm that 100% transmission of the L3T4 mutant takes place as determined by methods described below.

Analysis of DNA in Transgenic Mice

The transgene implanted in the eggs must be detectable in offspring transgenic mice in order to establish a transgenic mouse colony which expresses the L3T4 mutant gene. Thus, two protocols are devised to detect the presence of the L3T4 mutant in the transgenic mice.

The first protocol uses PCR analysis to detect L3T4 mutant sequences, but does not amplify wild type L3T4. This protocol is used as a qualitative measure for the introduction of mutant L3T4 into the murine genome.

The second protocol uses restriction fragment length polymorphism ("RFLP") analysis of genomic DNA. This protocol takes advantage of the fact that a new restriction enzyme site was created with oligonucleotide 1 (see Table I, used to make M1), which is diagnostic for the presence of the L3T4 mutant by a characteristic band by Southern blot analysis. This second protocol is a quantitative method for measuring the potential dosage of the integrated L3T4 mutant, and indicates whether the mice are heterozygous or homozygous. The quantitative measurement of this protocol is linked to the signal intensity observed by Southern blot analysis when compared to the intensity given by an internal control in all the samples, i.e., the wild type L3T4 DNA.

1. Discrimination Between Wild Type and Mutant L3T4

(a) PCR Analysis

Expression of mutant L3T4 in the tissues and organs of transgenic mice is measured by PCR analysis of tissue and organ-isolated mRNA (converted to cDNA) and DNA. The methods for DNA and RNA isolation are as described above except in the case of RNA isolation from organs, where polytron shearing and the guanidinium isothiocyanate method are used. See Chirgwin et al., Biochemistry 18:5294 [1979]. Oligonucleotide 5, shown in Table I, is used as the antisense primer while the sense primer encodes a sequence in the 5' untranslated region. This PCR fragment encodes a 340 base pair DNA. Oligonucleotide 5 is an excellent diagnostic measure for the presence of mutant L3T4 MRNA (cDNA) because the codons on the 3', end of this primer encode those mutations designed in oligonucleotide 1, rendering oligonucleotide 5 useless for PCR analysis of wild type L3T4. PCR amplification of mutant L3T4 cDNA is performed at 95° C. for 1 minute, 60° C. for 1 minute, and 72° C. for 30 seconds for cycles. We have successfully used these PCR primers and conditions to discriminate between mutant and wild type L3T4 cDNA and genomic DNA.

(b) RFLP Analysis

The oligonucleotide used to make mutant M1 and contained in all other mutants (see Table I) creates an Ava II restriction enzyme site. DNA isolated from transgenic mice tail biopsies is cut with Xho I and Ava II using conditions recommended by the enzyme supplier (L3T4 cDNA contains internal Xho I and Ava II sites). The DNA is separated by agarose gel electrophoresis and Southern blotted. The blot is then hybridized with a 300 base pair [$^{32}$P]-L3T4-labelled DNA probe which includes only L3T4 DNA from the L3T4 Xho I site in the 5' untranslated region to codon 35. This DNA probe hybridizes with the mutant L3T4 and wild type L3T4 DNA. The mutant L3T4 cut with Xho I-Ava II exhibits a 340 base pair hybridization band while the wild type shows a 680 base pair band. The signal intensity of these bands, measured by densitometry of the autoradiograms, are compared to estimate the relative dosage of the mutant L3T4 DNA in comparison to the wild type DNA. The heterozygosity/homozygosity of the transgenic mice is determined by comparing the signal intensity of known heterozygotes (some offspring of found mice matings) with the signal intensity of the heterozygote-heterozygote backcrosses; one quarter of the backcrossed mice should exhibit a doubling of the 340 base pair DNA signal indicating a transgenic mouse homozygous for the mutant L3T4. Quantitation is independent of the amount of DNA since the signal intensity of the diagnostic 340 base pair DNA can be normalized to the intensity of the wild type DNA.

2. Tissue and Organ Expression of Mutant 43T4

RNA is isolated from the spleen, thymus, peripheral blood cells, lymph nodes, bone marrow, pancreas, kidney, liver, heart and brain as described above, and converted to cDNA and analyzed by PCR analysis for the presence of L3T4 mutant RNA. Isolated RNA is pretreated with RNase-free DNase to destroy any contaminating DNA. FACS analysis to determine the cell surface expression of mutant L3T4 on isolated cells from the organs and tissues is performed as described above. T cells isolated from the spleen, thymus, and lymph nodes of transgenic mice homozygous for mutant L3T4 are analyzed by FACS analysis and $^{125}$I-gp120 binding.

In Vitro HIV-1 Infection of Transgenic Mouse Tissue

We determine the ability of HIV-1 to infect in vitro lymphoid tissues expressing L3T4 mutant receptors. The results indicate that L3T4 mutant expressed in a transgenic mouse can bind and facilitate HIV-1 infection of the mouse. More specifically, HIV-1 infections and analyses of the infections of lymphoid tissue from control heterozygous, and homozygous transgenic mice are performed essentially as described above. Experiments of longer term cultures (1–3 weeks) of stimulated cells include periodic measurement of supernatant p24 antigen and reverse transcriptase activity. These supernatants are also used as inocula to infect human CD4$^+$ peripheral blood lymphocytes.

Syncytium Assay

Splenic T cells from transgenic mice are isolated and tested for their ability to form syncytia with H-9/HTLV-IIIB cells by the methods as described abode.

OTHER EMBODIMENTS

The foregoing description has been limited to specific embodiments of this invention. It will be apparent, however, that variations and modifications may be made to the invention, with the attainment of some or all of the advantages of the invention.

For example, murine tissue culture cells which express L3T4 mutant protein can be used for screening potential AIDS drugs. Also, DNA sequences encoding L3T4 mutants can be used in the development of an mutant L3T4-toxin chimeric protein for destruction of HIV-1 infected cells expressing cell-surface HIV-1 gp120. In theory, mutant L3T4-toxin chimeric proteins could be targeted to HIV-1 infected cells expressing gp120 on the cell surface. These cells would find and internalize the chimera and be intoxicated by the toxin moiety.

Other embodiments are within the following claims.

What is claimed is:

1. A transgenic mouse whose cells express a transgene that contains a DNA sequence encoding a mutant L3T4 protein which, when expressed on the surface of a cell, facilitates entry into said cell by human immunodeficiency virus-1, wherein said mutant L3T4 protein comprises at least one amino acid residue substitution or deletion in a first segment corresponding to positions 49–54 of a native L3T4 protein so as to increase homology between said first segment and its counterpart in a CD4 protein, and wherein said entry results in low level transcription of human immunodeficiency virus-1 RNA in said cell.

2. The transgenic mouse of claim 1, wherein expression of said transgene is activated by a cell-specific regulatory element.

3. The transgenic mouse of claim 2, wherein said regulatory element is a CD3δ enhancer.

4. The transgenic mouse of claim 1, wherein said mutant L3T4 protein further comprises at least one amino acid residue substitution or deletion in a second segment corresponding to positions 39–44 of a native L3T4 protein so as to increase homology between said second segment and its counterpart in a CD4 protein.

5. The transgenic mouse of claim 4, wherein said mutant L3T4 protein further comprises at least one amino acid residue substitution or deletion in a third segment corresponding to positions 123–126 of a native L3T4 protein so as to increase homology between said third segment and its Counterpart in a CD4 protein.

6. The transgenic mouse of claim 5, wherein said mutant L3T4 protein further comprises at least one amino acid residue substitution or deletion in a fourth segment corresponding to positions 158–161 of a native L3T4 protein so as to increase homology between said fourth segment and its counterpart in a CD4 protein.

7. The transgenic mouse of claim 6, wherein said mutant L3T4 protein further comprises one amino acid substitution at position 57 of a native L3T4 protein so as to increase homology between amino acid residues at that position in the mutant protein and in a CD4 protein.

8. The transgenic mouse of claim 1, wherein said first segment is ProSerLysLeuAsn- (SEQ ID NO:1).

9. The transgenic mouse of claim 4, wherein said second segment is AsnGlnGly-SerPhe (SEQ ID NO:2).

10. The transgenic mouse of claim 5, wherein said third segment is ProProGly-.

11. The transgenic mouse of claim 6, wherein said fourth segment is GlyThrTrpThr (SEQ ID NO:3).

12. The transgenic mouse of claim 7, wherein said position 57 of said mutant protein is Ala.

13. The transgenic mouse of claim 8, wherein said second segment is AsnGlnGly-SerPhe (SEQ ID NO:2).

14. The transgenic mouse of claim 13, wherein said third and fourth segments are ProProGly- and GlyThrTrpThr (SEQ ID NO:3), respectively.

15. The transgenic mouse of claim 13, wherein the sequences of positions 1–38, 45–48, 58–122, 127–157, and 162–433 are identical to their counterparts in a native L3T4 protein and the sequences of positions 39–44, 49–54, 123–126, and 158–161 are AsnGlnGly-SerPhe (SEQ ID NO:2), ProSerLysLeuAsn- (SEQ ID NO:1), ProProGly-, and GlyThrTrpThr (SEQ ID NO:3), respectively.

16. The transgenic mouse of claim 4, wherein expression of said transgene is activated by a cell-specific regulatory element.

17. The transgenic mouse of claim 16, wherein said regulatory element is a CD3δ enhancer.

18. The transgenic mouse of claim 5, wherein expression of said transgene is activated by a cell-specific regulatory element.

19. The transgenic mouse of claim 18, wherein said regulatory element is a CD3δ enhancer.

20. The transgenic mouse of claim 6, wherein expression of said transgene is activated by a cell-specific regulatory element.

21. The transgenic mouse of claim 20, wherein said regulatory element is a CD3δ enhancer.

22. The transgenic mouse of claim 7, wherein expression of said transgene is activated by a cell-specific regulatory element.

23. The transgenic mouse of claim 22, wherein said regulatory element is a CD3δ enhancer.

* * * * *